US008173868B2

(12) United States Patent
Vainstein et al.

(10) Patent No.: US 8,173,868 B2
(45) Date of Patent: May 8, 2012

(54) TRANSGENIC PLANTS EXHIBITING INCREASED TOLERANCE TO STRESS AND METHODS OF GENERATING SAME

(75) Inventors: Alexander Vainstein, Rechovot (IL); Elena Shklarman, Rishon-LeZion (IL); Yael Leitner-Dagan, Kibbutz Naan Doar-Na Gezer (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 660 days.

(21) Appl. No.: 12/226,493

(22) PCT Filed: Apr. 29, 2007

(86) PCT No.: PCT/IL2007/000518
§ 371 (c)(1),
(2), (4) Date: Oct. 20, 2008

(87) PCT Pub. No.: WO2007/125531
PCT Pub. Date: Nov. 8, 2007

(65) Prior Publication Data
US 2009/0165171 A1    Jun. 25, 2009

Related U.S. Application Data

(60) Provisional application No. 60/795,181, filed on Apr. 27, 2006.

(51) Int. Cl.
*C12N 15/82* (2006.01)
(52) U.S. Cl. .................................................. 800/289
(58) Field of Classification Search .................... None
See application file for complete search history.

(56) References Cited

U.S. PATENT DOCUMENTS

| 7,479,267 B2 * | 1/2009 | Ogawa et al. ................. 424/9.2 |
| 2009/0165171 A1 | 6/2009 | Vainstein et al. | |
| 2010/0016166 A1 * | 1/2010 | Ogawa et al. ................ 504/320 |

FOREIGN PATENT DOCUMENTS

| WO | WO 98/24300 | * | 6/1998 |
| WO | WO 00/08188 | | 2/2000 |
| WO | WO 03/000898 | | 1/2003 |

OTHER PUBLICATIONS

Vishnevetsky et al (The Plant Journal (1999) 2094), 423-431.*
Tzfira et al (Plant Molecular Biology (Mar. 2005) 57:503-516).*
Office Action Dated Jan. 13, 2011 From the Israel Patent Office Re. Application No. 194911 and Its Translation Into English.
Communication Relating to the Results of the Partial International Search Dated Nov. 6, 2007 From the International Searching Authority Re.: Application No. PCT/IL2007/000518.
International Preliminary Report on Patentability Dated Nov. 6, 2008 From the International Bureau of WIPO Re.: Application No. PCT/IL2007/000518.
Communication Pursuant to Article 94(3) EPC Dated Feb. 10, 2009 From the European Patent Office Re.: Application No. 07736258.0.
Coutos-Thévenot et al. "In Vitro Tolerance to *Botrytis cinerea* of Grapevine 41B Rootstock in Transgenic Plants Expressing the Stilbene Synthase Vst1 Gene Under the Control of a Pathogen-Inducible PR 10 Promoter", Journal of Experimental Botany, XP002455480, 52(358): 901-910, 2001. Fig.7, Table 2.
Gillet et al. "Molecular Characterization of CDSP 34, A Chloroplastic Protein Induced by Water Deficit in *Solanum tuberosum* L. Plants, and Regulation of CDSP 34 Expression by ABA and High Illumination", The Plant Journal, 16(2): 257-262, 1998.
Langenkämper et al. "Accumulation of Plastid Lipid-Associated Proteins (Fibrillin/CDSP34) Upon Oxidative Stress, Ageing and Biotic Stress in Solanaceae and in Response to Drought in Other Species", Journal of Experimental Botany, XP002455396, 52(360): 1545-1554, 2001. p. 1548, r-h col.-p. 1549, 1-h col. Fig.3.
Leitner-Dagan et al. "CHRD, A Plant Member of the Evolutionarily Conserved YjgF Family, Influences Photosynthesis and Chromoplastogenesis", Planta, 225(1): 89-102, 2006.
Leitner-Dagan et al. "Expression and Functional Analyses of the Plastid Lipid-Association Protein CHRC Suggest Its Role in Chromoplastogenesis and Stress", Plant Physiology, 142(1): 233-244, 2006.
Manac'h et al. "Stress Induction of a Nuclear Gene Encoding for a Plastid Protein Is Mediated by Photo-Oxidative Events", Plant Physiology and Biochemistry, 37(11): 859-868, 1999.
Monte et al. "Leaf C40.4: A Carotenoid-Associated Protein Involved in the Modulation of Photosynthetic Efficiency?", The Plant journal, 19(4): 399-410, 1999.
Prändl et al. "HSF3, A new Heat Shock Factor From *Arabidopsis thaliana*, Derepresses the Heat Shock Respnse and Confers Thermotolerance When Overexpressed in Transgenic Plants", Molecular and General Genetics, XP002135096, 258: 269-278, 1998. p. 275.
Rey et al. "Over-Expression of a Pepper Plastid Lipid-Associated Protein in Tobacco Leads to Changes in Plastid Ultrastructure and Plant Development Upon Stress", The Plant Journal, 21(5): 483-494, 2000.
Suzuki et al. "Enhanced Tolerance to Environmental Stress in Transgenic Plants Expression the Transcriptional Coactivator Multiprotein Bridging Factor 1c$^1$[w]", Plant Physiology, XP002455481, 139(3): 1313-1322, 2005. Abstract.
Vellicce et al. "Enhanced Resistance to *Botrytis cinerea* Mediated by the Transgenic Expression of the Chitinase Gene CH5B in Strawberry", Transgenic Research, XP019269504, 15(1): 57-68, 2006. Fig.4.
Vishnevetsky et al. "Molecular Mechanisms Underlying Carotenogenesis in the Chromoplast: Multilevel Regulation of Carotenoid-Associated Genes", The Plant Journal, 20(4): 423-431, 1999.
Official Action Dated Mar. 24, 2011 From the US Patent and Trademark Office Re. U.S. Appl. No. 12/226,493.
International Search Report and the Written Opinion Dated Jan. 22, 2008 From the International Searching Authority Re.: Application no. PCT/IL2007/000518.

* cited by examiner

*Primary Examiner* — Anne Grunberg
*Assistant Examiner* — Lee Visone

(57) ABSTRACT

Methods of increasing tolerance of a plant to stress are provided. According to an exemplary aspect a method of increasing tolerance of a plant to a biotic stress is provided. The method comprising expressing within the plant an exogenous fibrillin/CDSP34 thereby increasing the tolerance of the plant to the biotic stress. Also provided are nucleic acid constructs and transgenic plants comprising same.

5 Claims, 10 Drawing Sheets
(3 of 10 Drawing Sheet(s) Filed in Color)

| SEQ ID No.3 | LeCHRC |
| SEQ ID NO.25 | Fib |
| SEQ ID NO.26 | CHRC |

```
LeCHRC    MASISSLNQHPCRTLQITSQYSKPTSKISTLPLSSTNFPSRTELHRAISVKEFTYPKEF   60
Fib       MASISSLNQHPCKTLQITSQYSK------ISSLPLTSPNFPSKTELRSISIKEFTNPKPKF  56
CHRC      MAEVSQFNQLPCKTLALNPPQPQ-----LTSKPSVFP-IASIGATARAAGKSLISVRPAE   55
          ** :*: ***:** * :*** *       ::** :* *  *  ::    ..*:: *.::

LeCHRC    TAQATNYDKEDEWGPEVEKIS--PGGVAVVD--EEPPKEPSEIELLKKQLADSFYGTNRG  116
Fib       TAQATNYDKEDEWGPELEQIN--PGGVAVVE--EEPPKEPSEMEKLIKKQLTDSFYGTNRG  112
CHRC      KVRAVLND--DEWGEDKDEKYGDDSSYAVAEEKEEEKPLEPSEIYKLKKALVDSFYGTDRG  113
           . *  :*  :**  :.:        .***:  :: :* ****: :: *.* ****:**

LeCHRC    LSASSETRAEIVELITQLESKNPNPAPTEALTLLNGKWILAYTSFSGLFPLLSRGNLLLV  176
Fib       LSASSETRAEIVELITQLESKNPTPAPTEALSLLNGKWILAYTSFSGLFPLLARGNLLPV  172
CHRC      LRVSRDTRAEIVELITQLESKNPTPAPTEALTLLNGKWILAYTTFAGLFPLLSR-NLPLV  172
          *   . ****************.********:**********:*:****** *  ** *

LeCHRC    RVEEISQTIDSESFTVQNSVVFAGPLATMSISTNAKFEVRSPKRVQIKFEEGIIGTPQLT  236
Fib       RVEEISQTIDAETLIVQNSVVFAGPLSTTSISTNAKFEVRSPKRLQINFEEGIIGTPQLT  232
CHRC      KVEEISQTIDSENLTVQNSVQFSGPLATTSITTNAKFEVRSPLRVHIKFEEGVIGTPQLT  232
          :*********:*. .***** *:***:*.**:********** *::*:****:******

LeCHRC    DSIVLPENVEFLGQKIDLSPFKGLITSVQDFASSVAKSISSQPFIKFPISNNNAQSWLLT  296
Fib       DSIELPENVEFLGQKIDLSPFKGLITSVQDTATSVAKSISSQPPIKFPISNSYAQSWLLT  292
CHRC      DSIVIPDNVDFLGQKIDFTPFNGIIISSLQDTASNVAKTISSQPIKFSISNTRVESWLLT  292
          ***.:*:**:******:.**:*:* *. *:*:.***:**** **:***.  :.*****

LeCHRC    TYLDDELRISRGDAGSVFVLIKEGSPLLKP  326
Fib       TYLDAELRISRGDAGSIFVLIKEGSPLLKP  322
CHRC      TYLDEDLRISRGDGGSVFVLLKEGSSFLSL  322
          ****  *******.**:***:***** *.
```

Fig. 1

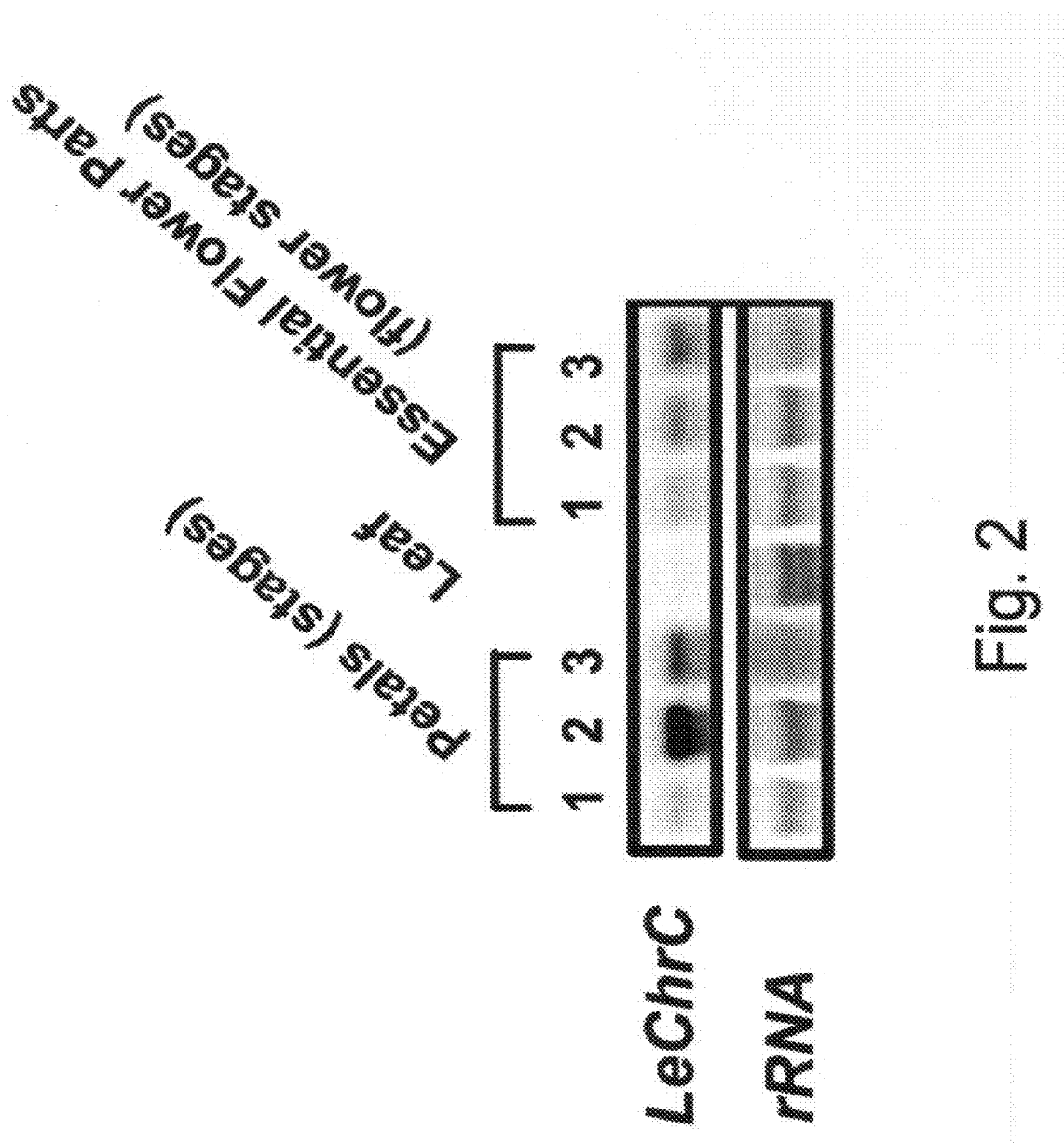

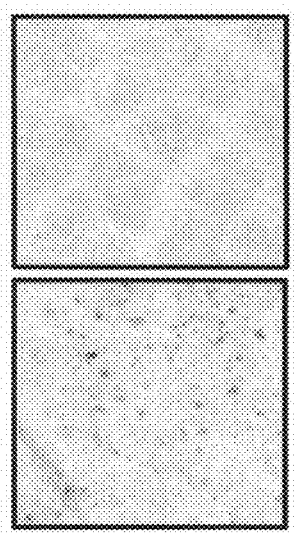
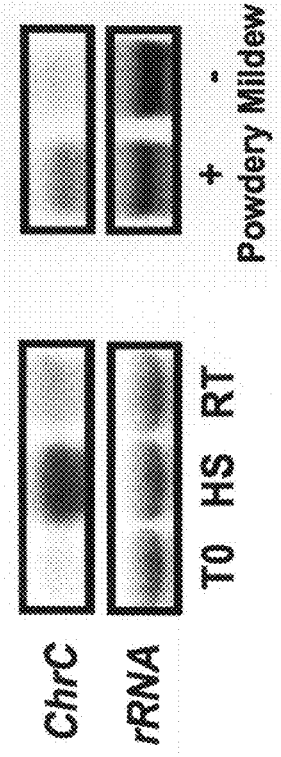
ChrC::GUS
Fig. 3a
Fig. 3b
Fig. 3c

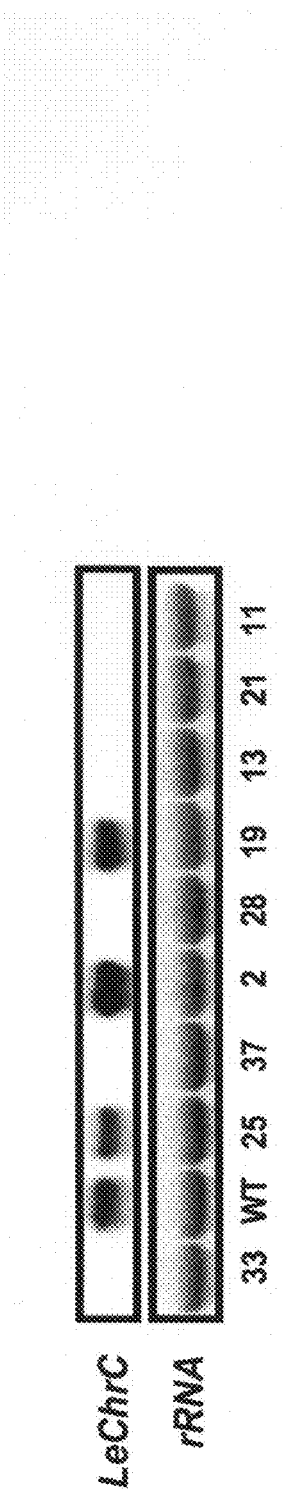
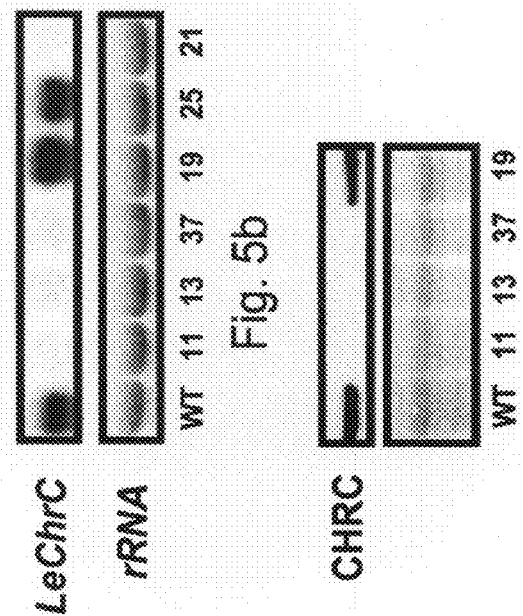
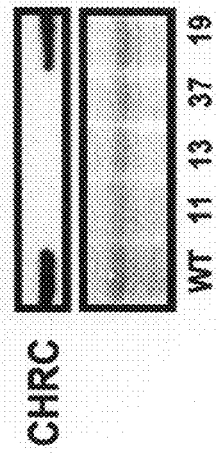
Fig. 5a
Fig. 5b
Fig. 5c

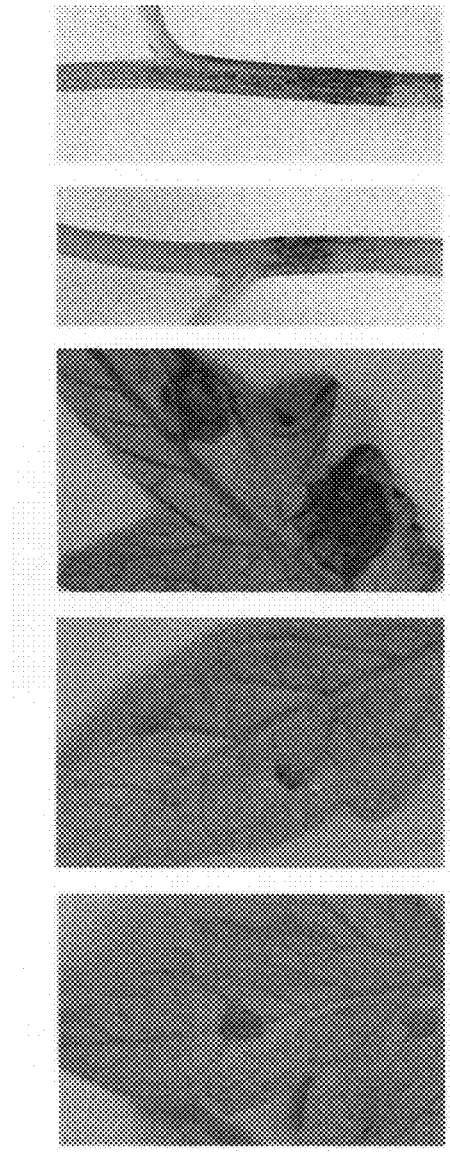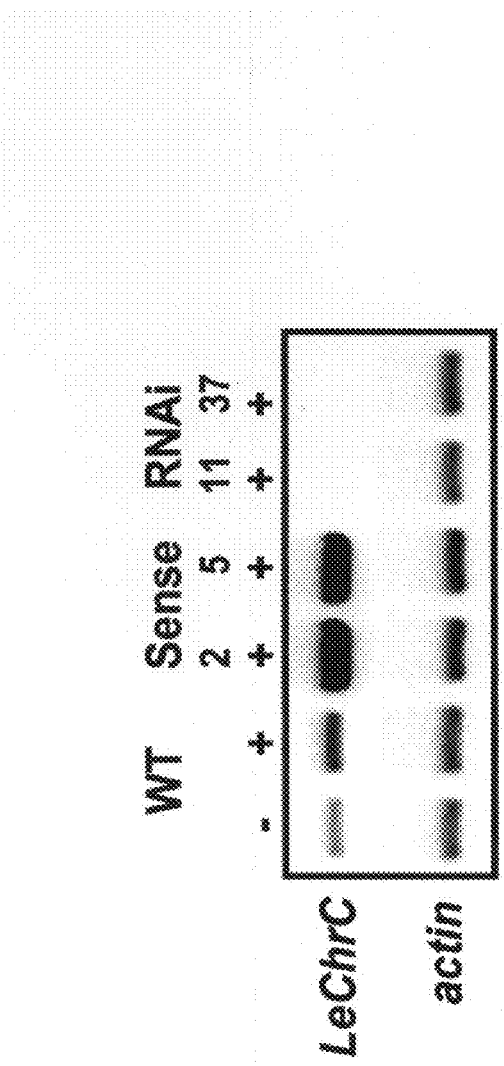

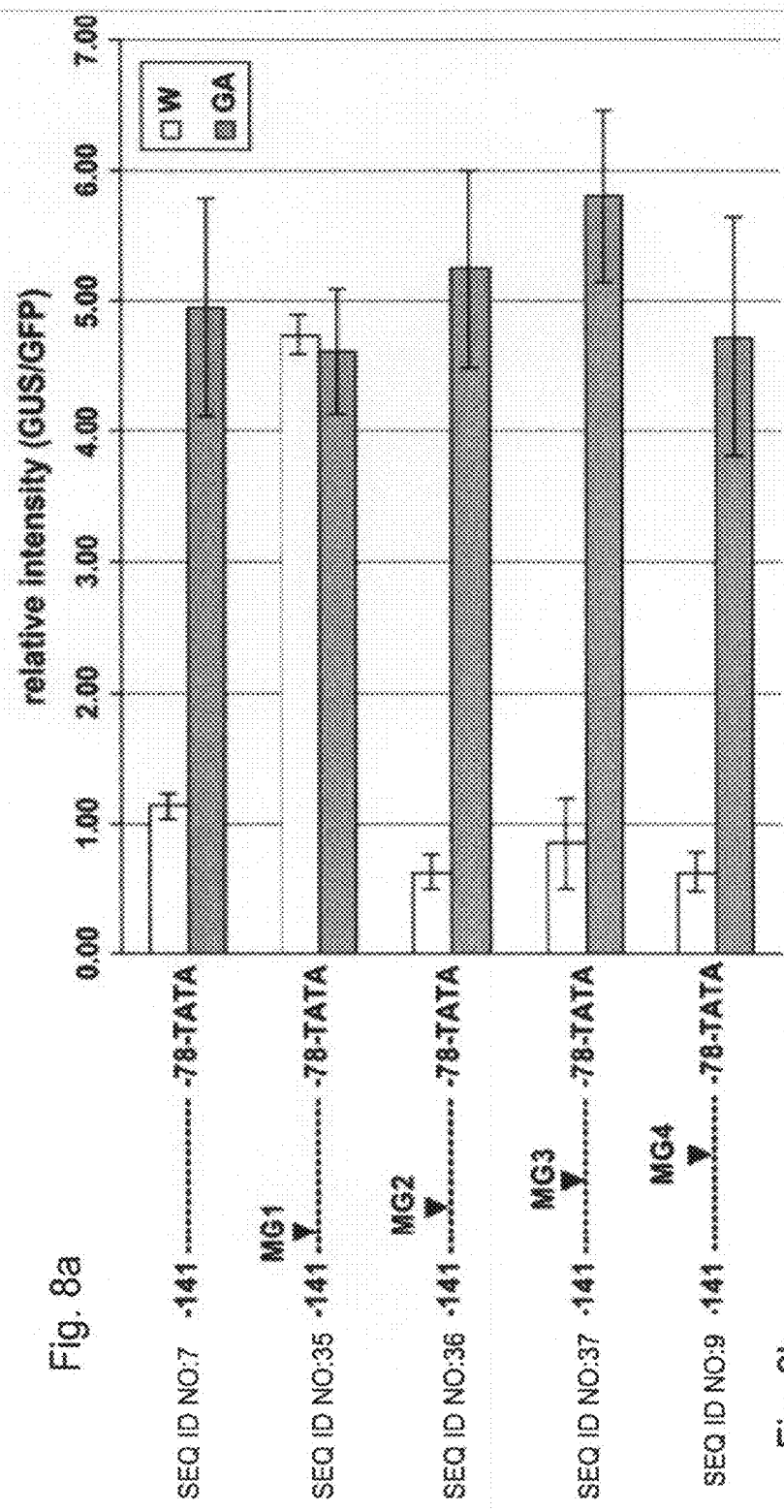

Fig. 9a

SEQ ID NO: 28, 29, DQ311672

Fig. 9b

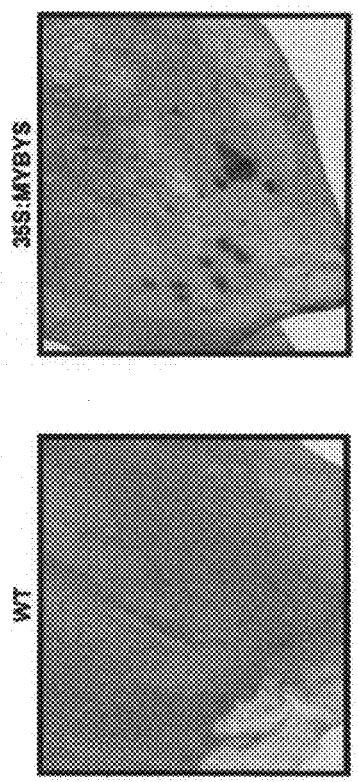
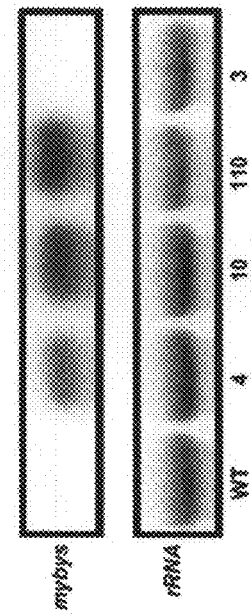
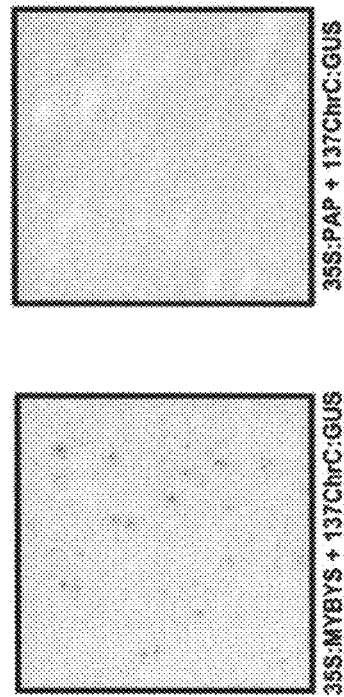
Fig. 10a
Fig. 10b
Fig. 10c

TRANSGENIC PLANTS EXHIBITING INCREASED TOLERANCE TO STRESS AND METHODS OF GENERATING SAME

RELATED APPLICATIONS

This application is a National Phase of PCT Patent Application No. PCT/IL2007/000518 having International filing date of Apr. 29, 2007, which claims the benefit of U.S. Provisional Patent Application No. 60/795,181 filed on Apr. 27, 2006. The contents of the above Applications are all incorporated herein by reference.

FIELD AND BACKGROUND OF THE INVENTION

The present invention relates to transgenic plants exhibiting increased tolerance to stress and methods of generating same.

Modern agriculture strives to achieve the highest possible crop yields in order to overcome the continuously growing land limitation. Uniformity, as well as growth density, render modern crops susceptible to quickly spreading damage of many pathogens such as nematodes, bacteria, fungi, viruses, viroids, and phytoplasms. A growing resistance exists to the use of chemical pesticides due to many disadvantages brought forth by chemical abuse including negative environmental effects, and diminishing affectivity. For example, the magnitude of fungicidal treatments has provoked the appearance of resistant strains, necessitating the development of new treatments (Leroux et al., *Pest Manag. Sci.* 58:876, 2002). On the other hand, fighting pathogens by utilizing the biological inert, plant mechanisms is environmentally safer, and less prone to become ineffective by the creation of resistant pathogens.

An example of a damaging plant pathogen is *B. cinerea*. This phytopathogenic fungi has a broad host range, of more than 200 plant species, including tomato (Elad et al., In: *Botrytis: Biology, Pathology and Control*, Kluwer Academic Publishers, Dordrecht, The Netherlands, pp. 1-8, 2004). *B. cinerea* cause rapid destruction of the host plant tissues as it proceeds to colonize it (a pathology called necrotrophy). Together with other filamentous fungi, it is considered to be the principal pathogenic agents of plants. Estimated losses for vineyards in France amount to 15-40% of the harvest, depending on climatic conditions. Other losses are estimated at 20-25% of the strawberry crops in Spain and cut flowers in Holland. Fungicidal treatments against *B. cinerea* cost about 540 million euros in 2001, which represents 10% of the world fungicide market (Annual Report, UIPP, 2002). Other plant pathogens are viruses, e.g., the tobacco mosaic virus (TMV), the potato virus Y (PVY) and tomato yellow leaf curl virus (TYLCV). Plant virus diseases pose severe constraints to the production of a wide range of economically important crops worldwide (Agrios, G N, Plant Pathology. fourth ed. Academic Press, Inc., San Diego, Calif., 1997). Some estimates put total worldwide damage due to plant viruses as high as $6 \times 10^{10}$ US$ per year. Diseases caused by plant viruses are difficult to manage and their control mainly involves the use of insecticides to kill insect vectors, the use of virus-free propagating materials, and the selection of plants with appropriate resistance genes. Virus-free stocks are obtained by virus elimination through heat therapy and/or meristem tissue culture, but this approach is ineffective for viral diseases transmitted by vectors. While vectors can be controlled by insecticides, often the virus has already been transmitted to the plant before the insect vector is killed. The use of resistant cultivars has been the most effective means of control, however plant virus resistance genes are frequently unavailable and their introgression into some crops is not straightforward.

Abiotic stress (also referred to as "environmental stress") conditions such as salinity, drought, flood, suboptimal temperature and toxic chemical pollution, are additional major factors which cause substantial damage to agricultural plants. Most plants have evolved strategies to protect themselves against these conditions. However, most of the crop plants are very susceptible to abiotic stress, and thus necessitate optimal growth conditions for commercial crop yields. Furthermore, crop plants are in numerous times grown outside of the climate from which they originate. The unnatural conditions, together with the sensitivity of crop plants, effect plant development and growth which result in a less then optimum yield. An example of abiotic stress is excessive heat, which, in most times, is linked to drought. Germination of many crops is very sensitive to temperature. Seedlings and mature plants that are exposed to excess heat may experience heat shock, which may arise in various organs, including leaves and particularly fruit, when transpiration is insufficient to overcome heat stress. Heat also damages cellular structures, including organelles and cytoskeleton, and impairs membrane function (Buchanan et al., in Biochemistry and Molecular Biology of Plants, American Society of Plant Physiologists, Rockville, Md., 2000). Heat shock may produce a decrease in overall protein synthesis, accompanied by expression of heat shock proteins.

Plastid lipid-associated proteins, also termed fibrillin/CDSP34 proteins, are part of protein-lipid structures residing in fibrillar-type chromoplasts, such as those of flowers and ripening fruit, as well as in other plastids. For example, ChrC, a 35-kD carotenoid-associated PAP, was found to be expressed in chromoplasts of fruit and flower tissues of the yellow cucumber, *Cucumis sativus* (Vainstein et al., *Plant Physiol.* 104, 321-326, 1994; Vishnevetsky et al., *Plant J.* 10, 1111-1118, 1996). PAPs, like the Cucumber ChrC and, the pepper PAP Fib, are known to accumulate at both protein and transcript levels, in parallel to carotenoid pigment accumulation, as part of the differentiation of chloroplasts to non photosynthetic chromoplasts (chromoplastogenesis), and in concomitance with fibril development (Deruere et al., *Plant Cell* 6, 119-133, 1994). Interestingly, PAPs, like the potato CDSP34 and pepper fibrillin, were found to be overexpressed upon induction of abiotic stresses e.g., oxidative stress, light, salt, wound, aging and drought [examples can be found in Chen et al., *Plant J.* 14, 317-326, 1998; Langenkämpel et al., *J Exp Bot* 52(360): 1545-1554 (2001); Murphy D J, *Proceedings of the 16th International Plant Lipid Symposium*, Budapest, pp. 55-62, 2004]. Elevation of expression of PAP upon stress induction was also evidenced in experiments showing higher expression of exogenous promoters in transgenic plants; for example, the expression of the fibrillin promoter in transgenic tomato plants was elevated during bacterial (*Erwinia* strains) infections [Langenkämpel et al., J Exp Bot 52(360): 1545-1554 (2001)] and during the induction of abiotic stresses e.g., drought, cold, salt, light and herbicides (Manac'h and Kuntz, Plant Physiol. Biochem. 37, 859-868, 1999). Hence, it is suggested that PAP expression is increased upon abiotic stress but no direct evidence is provided showing that PAP may confer resistance and is not, a mere "by product" of stress induction.

Indeed, up to date, overexpression of Fib in transgenic tobacco, and fibrillin in fibrillin overexpressing *Arabidopsis* lines, was merely found to improve plant performance under induced light stress conditions (Rey et al., Plant J. 21, 483-494 2000; Yang et al., PNAS 103: 6061-6066, 2006). No other support was provided to date regarding the ability of PAP to confer tolerance to other abiotic stress, needless to say to biotic stress.

The cucumber ChrC promoter was characterized and used to develop products for increasing accumulation and sequestration of carotenoids in plants and bacteria (U.S. Pat. No. 6,551,793). Two factors were found to activate the ChrC promoter. The first, $GA_3$, which plays a critical role in chromoplastogenesis, was found to lead to enhanced carotenoid accumulation as well as to transcriptional activation of ChrC expression. The response to GA was localized to a 290-bp fragment within the ChrC promoter (Vishnevetsky et al., Plant J. 20, 423-431, 1999; Sutoh K and Yamauchi D, Plant J. 34, 635-645, 2003). Another activator of the ChrC promoter, a myb-like factor termed MYBYS, was recently characterized, and harnessed to develop a modular series of plasmids for autofluorescent protein tagging and expression of multiple genes in plants (Tzfira et al., Plant Mol. Biol. 57, 503-516, 2005).

Use of the ChrC promoter was also suggested for inducing flower-specific expressed genes in the genus Targets (U.S. Patent Application 0060162020).

In none of the abovementioned studies, however, was the use of the coding sequence of PAPs suggested for improving plant pathogen resistance, nor was the use of the PAP or PAP expression activators, suggested for conferring abiotic stress resistance excluding light resistance.

There is thus a widely recognized need for, and it would be highly advantageous to have, constructs for conferring resistance to stress.

SUMMARY OF THE INVENTION

According to one aspect of the present invention there is provided a method of increasing tolerance of a plant to a biotic stress, the method comprising expressing within the plant an exogenous fibrillin/CDSP34 thereby increasing the tolerance of the plant to the biotic stress.

According to another aspect of the present invention there is provided a method of increasing tolerance of a plant to a biotic or an abiotic stress, the method comprising expressing within the plant an exogenous MYBYS thereby increasing the tolerance of the plant to the biotic or the abiotic stress.

According to still further features in the described preferred embodiments the method further comprising expressing within the plant an exogenous MYBYS, so as to increase the fibrillin/CDSP34 expression in the plant.

According to still further features in the described preferred embodiments the method further comprising subjecting the plant to gibberellin, so as to increase the fibrillin/CDSP34 expression in the plant.

According to still further features in the described preferred embodiments the expressing within the plant an exogenous fibrillin/CDSP34 is effected by introducing to the plant, an exogenous nucleic acid construct comprising a nucleic acid sequence encoding fibrillin/CDSP34 and at least one promoter capable of directing transcription of the nucleic acid sequence in the plant or plant cell.

According to still further features in the described preferred embodiments the fibrillin/CDSP34 is set forth in SEQ ID NO: 3 or 26.

According to still further features in the described preferred embodiments the MYBYS is set forth in SEQ ID NO: 29.

According to still further features in the described preferred embodiments the expressing is effected by introducing to the plant, an exogenous nucleic acid construct comprising a nucleic acid sequence encoding MYBYS, and at least one promoter capable of directing transcription of the nucleic acid sequence in the plant or plant cell.

According to yet another aspect of the present invention there is provided a method of increasing tolerance of a plant to a heat shock stress, the method comprising: (a) upregulating an expression of fibrillin/CDSP34 in the plant (b) growing the plant under heat shock conditions, thereby increasing tolerance of the plant to heat shock stress.

According to still further features in the described preferred embodiments the upregulating is effected by contacting the plant with an agent selected from the group consisting of gibberellin (GA), an exogenous nucleic acid sequence encoding MYBYS and an exogenous nucleic acid sequence encoding fibrillin/CDSP34.

According to still further features in the described preferred embodiments the MYBYS is set forth in SEQ ID NO: 29.

According to still further features in the described preferred embodiments the fibrillin/CDSP34 is set forth in SEQ ID NO: 3 or 26.

According to still another aspect of the present invention there is provided a nucleic acid construct comprising a cis acting regulatory element being no longer than 500 nucleic acids in length, the cis acting regulatory element comprising a nucleic acid sequence set forth in SEQ ID NO: 32.

According to an additional aspect of the present invention there is provided a host cell comprising the nucleic acid construct.

According to still further features in the described preferred embodiments the host cell is a plant cell.

According to yet an additional aspect of the present invention there is provided a transgenic plant comprising the nucleic acid construct.

According to still further features in the described preferred embodiments the method further comprising growing the plant under biotic stress conditions.

According to still further features in the described preferred embodiments the method further comprising growing the plant under abiotic stress conditions.

According to still an additional aspect of the present invention there is provided a method of inducing expression of an exogenous gene of interest in a plant the method comprising: (a) transforming the plant with a nucleic acid construct comprising a nucleic sequence encoding the gene of interest, the nucleic acid sequence comprising a cis acting regulatory element for directing expression of the gene of interest, the nucleic sequence being no longer than 1000 nucleic acids in length and comprising a nucleic acid sequence set forth in SEQ ID NO: 32, to thereby obtain a transgenic plant; and (b) subjecting the transgenic plant to gibberellin (GA), thereby inducing the expression of the gene of interest in the plant.

According to a further aspect of the present invention there is provided a transgenic plant comprising a nucleic acid sequence encoding an amino acid sequence being at least 90% homologous to SEQ ID NO: 29, the amino acid sequence being operably linked to an inducible promoter.

According to yet a further aspect of the present invention there is provided a nucleic acid construct comprising a nucleic acid sequence encoding an amino acid sequence being at least 90% homologous to SEQ ID NO: 29 the amino acid sequence being operably linked to an inducible promoter.

According to still further features in the described preferred embodiments the biotic stress is selected from the group consisting of a nematode infection, a bacterial infection, a fungal infection, a viral infection, a viroidal infection and a phytoplasm infection.

According to still further features in the described preferred embodiments the abiotic stress is selected from the group consisting of salinity, aging, herbicidal, drought, flood, high temperature, low temperature, oxidative stress, heavy metal toxicity, wound, light, anaerobiosis chemical nutrient deficiency, nutrient excess, atmospheric pollution and irradiation.

According to still further features in the described preferred embodiments the at least one promoter is a plant promoter.

According to still further features in the described preferred embodiments the at least one promoter is a constitutive promoter.

According to still further features in the described preferred embodiments the constitutive promoter is CaMV 35S promoter.

According to still further features in the described preferred embodiments the at least one promoter is an inducible promoter.

According to still further features in the described preferred embodiments the inducible promoter is an abiotic stress inducible promoter.

According to still further features in the described preferred embodiments the inducible promoter comprises a cis acting regulatory element being no longer than 1000 nucleic acids in length, the cis acting regulatory element comprising a nucleic acid sequence set forth in SEQ ID NO: 32.

According to still further features in the described preferred embodiments the expressing is effected by infecting the plant with a virus comprising the fibrillin/CDSP34 and/or MYBYS.

According to still further features in the described preferred embodiments the virus is an avirulent virus.

The present invention successfully addresses the shortcomings of the presently known configurations by providing transgenic plants exhibiting increased tolerance to stress and methods of generating same.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 1 is a multiple sequence alignment of the ChrC homologue amino-acid sequences, *Lycopersicon esculentum* LeChrC (SEQ ID NO. 3), *Capsicum annuum* Fib (SEQ ID NO. 25) and *Cucumis sativus* ChrC (SEQ ID NO. 26), performed with CLUSTAL W (Thompson et al., Nucl. Acid. Res. 22, 4673-4680, 1994). The transit peptide, which directs the ChrC protein to the plastid is underlined. Identical residues in the column are marked with an asterisk (*), and conserved (:) and semi-conserved (.) substitutions are indicated.

FIG. 2 is an RNA blot image depicting temporal and spatial regulation of LeChrC. Total RNA extracted from tomato tissues, at different developmental stages, was probed with radiolabeled LeChrC. Note LeChrC is expressed in flower petals and not in leaves, and more at developmental stages 2 and 3 (48 and 12 hours before anesthesis, respectively).

FIGS. 3a-c depict induction of ChrC expression in cucumber leaves by biotic and abiotic stresses. FIGS. 3a-b are photo images depicting activation of the ChrC promoter by heat shock (FIG. 3a) and fungal inoculation (FIG. 3b). Cucumber leaves were cultured in vitro for 4 hours at 42° C. (HS) or room temperature (RT). In addition, leaves from plants infected (+) with powdery mildew *Sphaerotheca fuliginea* (*Oidium* sp.) were compared to control uninfected leaves (−). Following bombardment with ChrC:GUS, leaves were histochemically analyzed for GUS expression. FIG. 3c is an RNA-blot image depicting the effect of heat shock and fungal inoculation on ChrC transcript levels. Total RNA was extracted from detached leaves (T0), and from leaves heat shock treated as described above. Following blotting, RNA was probed with radiolabeled ChrC. Note the elevation in ChrC transcript levels following fungal or heat induced stress.

Figure 4B:
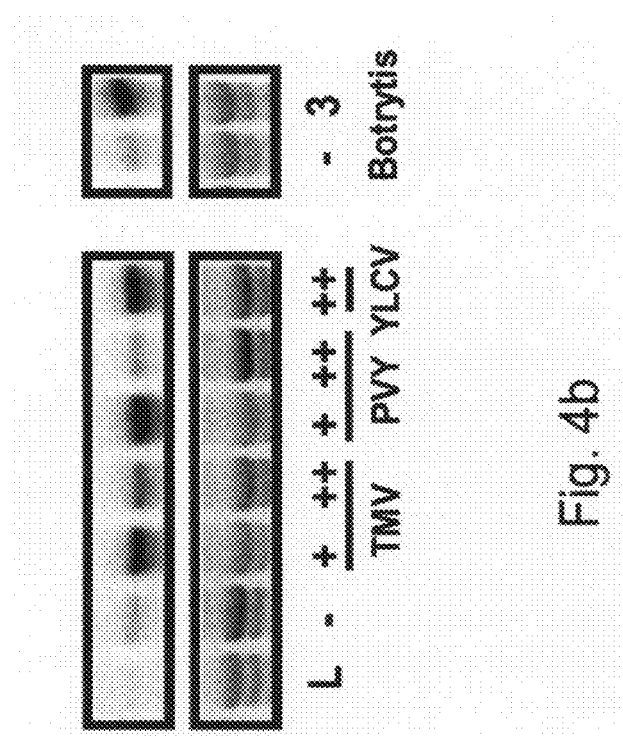
Figure 4A:
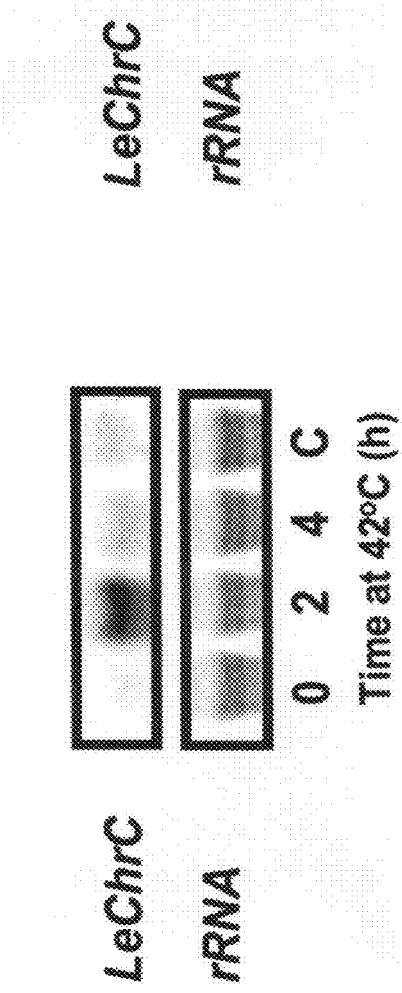

FIGS. 4a-b are RNA-blot images depicting induction of LeChrC transcript levels by abiotic and biotic (pathogen, FIG. 4b) stresses. FIG. 4a shows induction of LeChrC transcript levels following abiotic stress effected by heat shock. Total RNA was extracted from tomato leaves cultured at room temperature for 4 h (control plants, C) or tomato leaves cultured in vitro at 42° C. for 0-4 hours. FIG. 4b shows induction of LeChrC transcript levels by biotic stress effected by pathogen infection. Total RNA was extracted from leaves taken from plants three days (3), a week (+) and two weeks (++) after inoculation with the viruses TMV, PVY and TYLCV, with the fungus *Botrytis cinerea*, from mock-inoculated plants (−) or from plants prior to infection (L). Following treatment, RNA was blotted and probed with radiolabeled LeChrC. Note higher levels of LeChrC transcript following viral, fungal or heat induced stress.

FIGS. 5a-c are RNA-blot images depicting molecular analysis of transgenic tomato plants with suppressed LeChrC expression. FIG. 5a depicts analysis of total RNA from flowers with suppressed LeChrC generated via the RNAi approach. Total RNA from stage 2 corollas was extracted and probed with radiolabeled LeChrC. Analysis was performed on T0 (FIG. 5a) and T2 (FIG. 5b) generations of RNAi LeChrC-transgenic plants (lines 11, 13, 21, 28, 33, 37) vs. control transgenic lines with no suppression (lines 2, 19, 25) and control non-transgenic (WT) tomato plants. Proteins from stage 2 corollas of the T2 generation were also extracted and analyzed by western blotting using antibodies against ChrC (FIG. 5c).

FIGS. 6a-f depict susceptibility of transgenic tomato plants with modulated ChrC expression levels to *Botrytis cinerea* infection. Transgenic tomato overexpressing ChrC (sense, transgenic lines 2, 5), control non-transgenic (WT) and RNAi LeChrC-suppressed plants (RNAi lines 11, 37) were infected with *B. cinerea*. FIGS. 6*a-e* depict photo images of *B. cinerea* disease symptoms 6 days following inoculation, in control non transgenic leaves (FIG. 6*a*), transgenic sense leaves (FIG. 6*b*), and transgenic RNAi leaves (FIG. 6*c*), and disease symptoms in stems 8 days after inoculation of control non transgenic plants (FIG. 6*d*) and transgenic RNAi plants (FIG. 6*e*). FIG. 6*f* is an RT-PCR image depicting expression of LeChrC, and control gene actin, in non transgenic (WT), transgenic sense, and transgenic RNAi leaves prior to infection (−) or 3 days after infection (+) with *B. cinerea*.

Figure 7A:
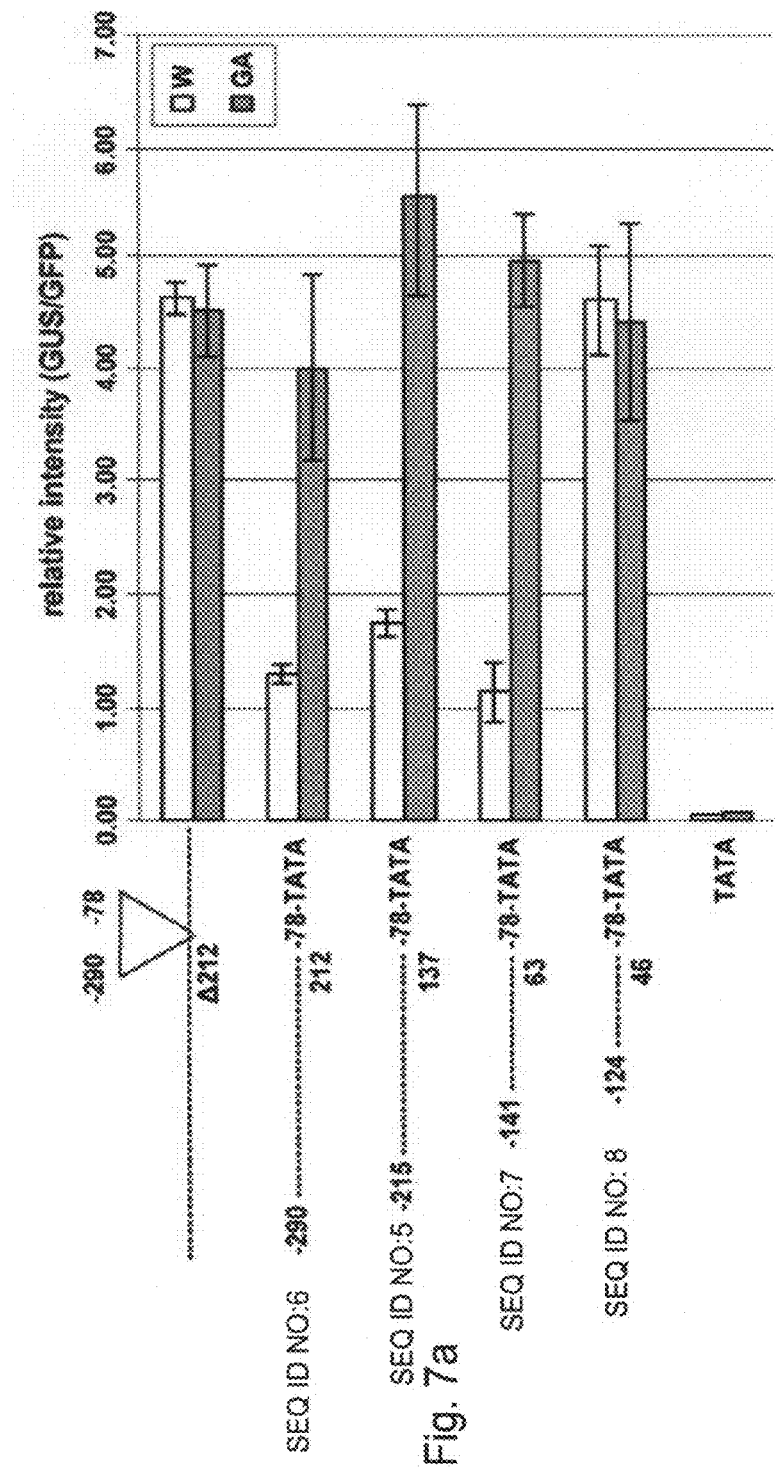
Figure 7B:
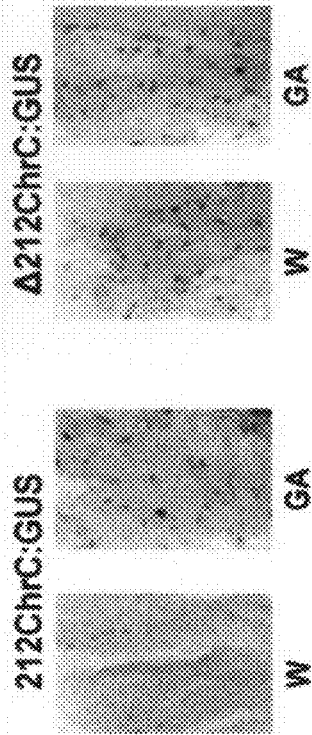

FIGS. 7*a-b* are images depicting the identification of $GA_3$-responsive cis-elements in the ChrC promoter region. FIG. 7*a* is a bar graph depicting GUS expression in stage 1 cucumber corollas grown in vitro without (W, white bars) or with (GA, grey bars) $GA_3$, that were cobombarded with 35S:GFP and different ChrC promoter fragments fused to GUS via the 35S minimal promoter (TATA). GUS expression was normalized to the GFP signal using ImageJ software. The results of five replicates± SE are presented. FIG. 7*b* shows photo image histochemical visualizations of GUS activity in stage 1 cucumber corollas grown in vitro without (W) or with $GA_3$ (GA), following bombardment with ChrC promoter lacking 212 bp (−290 to −78) fused to GUS (Δ212ChrC:GUS) or the 212-bp fragment of the promoter (−290 to −78) fused to GUS via an 35S minimal promoter (212ChrC:GUS). Note expression is elevated, when the whole 212 bp fragment (FIGS. 7*a* and *b*), or the maximal fraction of this fragment (−290 to −124, FIG. 7*a*) is missing from the promoter sequence, indicating a repressor-mediated regulation of the ChrC promoter by $GA_3$, which interacts with an element residing in the 18 bp fragment (between −141 and −124; SEQ ID NO: 32) of the promoter region.

FIGS. 8*a-b* depict the effect of mutations on $GA_3$ responsiveness of the ChrC promoter. FIG. 8*a* is an illustration of the mutated region of the ChrC promoter. The 6-bp sequence GTA TCT was used to replace the original sequence of the promoter, with three-base gaps between each of the four (MG1-MG4) mutations. FIG. 8*b* is a bar graph depicting GUS expression in stage 1 cucumber corollas grown in vitro without (W, white bars), or with (GA, grey bars) $GA_3$, that were cobombarded with 35S:GFP and different ChrC promoter fragments, original and mutated, fused to GUS via an 35S minimal promoter (TATA). GUS expression was normalized to the GFP signal using ImageJ software. The results of five replicates±SE are presented. Note the MG1 construct containing a mutation between −138 and −133, yielded similarly high GUS expression in both water- and $GA_3$-treated corollas, indicating that the bases CTC, between −138 and −136 are necessary elements for the response of ChrC promoter to $GA_3$ activation.

Figures 9A, 9B:
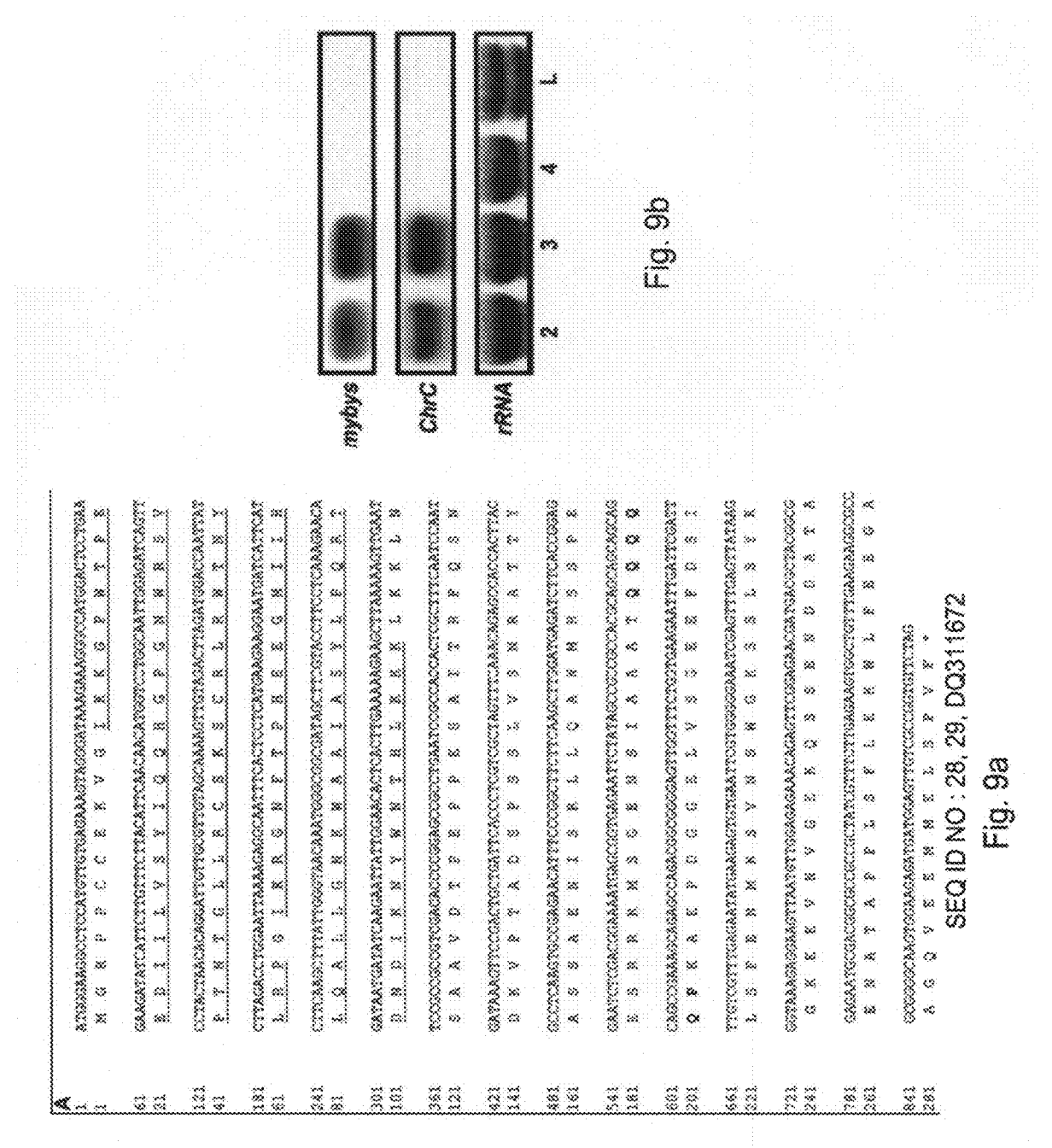

FIGS. 9*a-b* show molecular and transcriptional analysis of MYBYS. FIG. 9*a* is an illustration of the nucleotide and predicted amino acid sequences of MYBYS, showing the conserved R2/R3 DNA-binding domains at the 5' end of the MYBYS sequence in underline and a typical, Gln and Pro rich activation domain at the 3' end in bold. The terminal codon is marked with an asterisk. FIG. 9*b* is an RNA-blot image depicting temporal and spatial regulation of mybys transcript levels in cucumber tissues. Total RNA extracted from cucumber leaves (L) and corollas at different developmental stages (stages 2, 3 and 4; 72, 24 days before, and during anethesis, respectively) was probed with a radiolabeled fragment of mybys specific to the 3' end of the gene. The same RNA blot was rehybridized with radiolabeled ChrC. Note similar transcription levels of mybys and ChrC.

FIGS. 10*a-c* depict MYBYS transcription factor specifically activates the ChrC promoter. FIG. 10*a* shows histochemical visualization of GUS activity in petunia flowers bombarded with ChrC:GUS alone, or ChrC:GUS or 137ChrC:GUS (containing GUS driven by 3,500 or 137 bp of the ChrC promoter, respectively) cobombarded with 35S: MYBYS. In control cobombardment experiments, MYBYS was replaced by another MYB factor, PAP, which regulates the anthocyanin pathway (35S:PAP). FIG. 10*b* shows Histochemical visualization of GUS activity in nontransgenic (WT), or transgenic young green tomato flowers constitutively expressing 35S:MYBYS (line 10), following bombardment with ChrC:GUS. FIG. 10*c* is an RNA-blot image showing accumulation of mybys in 35S:MYBYS transgenic tomato flowers (independent transgenic lines 4, 10, and 110). RNA-blot analysis was performed using radiolabeled 3' mybys as a probe. A nontransgenic line (WT) and a transgenic line with no expression of MYBYS (line 3) were used as controls.

DESCRIPTION OF THE PREFERRED EMBODIMENTS

The present invention is of transgenic plants exhibiting endurance to various stress conditions as well as methods of generating same.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Modern agriculture is constantly on the look for novel methods and compositions that enable growing crops at locations which are less than optimal. Conversely, modern crops are frequently increasingly susceptible to biotic and abiotic stress conditions due to genomic uniformity and growth density of these crops. There is thus a growing need for methods and compositions which render plants tolerant to biotic and abiotic stresses, which do not include the use of pesticides and other environmentally damaging chemicals.

The chromoplastogenesis related family of the plastid lipid associated proteins (PAPs, or fibrillin/CDSP34) were previously found to be stress induced. There is no direct evidence, however, that PAP may confer tolerance to stress, apart from the findings that PAP over-expression in transgenic lines, improved plant performance under induced light stress conditions (Rey et al., Plant J. 21, 483-494 2000; Yang et al., PNAS 103: 6061-6066, 2006). No other support was provided to date regarding the ability of PAP to confer tolerance to other abiotic or biotic stress.

While reducing the present invention to practice the present inventor has uncovered that PAP (i.e., fibrillin/CDSP34, ChrC, as further described hereinbelow) expression can be used to increase resistance of plants to biotic stress. The present inventor has demonstrated a transcriptional regulation of ChrC expression by gibberellins (GA) and MYBYS, suggesting the use of this PAP regulatory pathway in conferring resistance to various stress conditions.

As is illustrated hereinbelow and in the Examples section which follows, the present inventor has cloned a tomato ChrC sequence (LeChrC, SEQ ID NO: 2, GenBank Accession NO. DQ310151) from a tomato petal cDNA library. Endogenous expression of LeChrC was found to be developmentally and spatially regulated (see FIG. 2) in resemblance to the cucumber ChrC. Activation of ChrC expression under biotic stress conditions was demonstrated upon infection with Botrytis and Powdery Mildew and various viruses (see FIGS. 3a-c and 4b). In addition, the ChrC was found to be temperature regulated (FIG. 4a). The critical role of ChrC in inducing tolerance to biotic stress was evidenced by gene silencing assays, whereby, RNAi-suppressed LeChrC exhibited accelerated susceptibility to Botrytis infection (Example 2), as compared to wild type plants and ChrC over-expressing tomato plants.

Structural-functional analysis of ChrC promoter sequence revealed a minimal regulatory element for conferring inducibility (e.g., GA). A minimal constitutive and inducible activity of ChrC promoter sequence was also characterized (SEQ ID NO: 8 and 7, respectively). The inducible activity of the promoter was further characterized to reside within a 18 bp sequence in the minimal inducible promoter fragment (SEQ ID NO: 32), and furthermore, the 3 nucleic acids responsible for the inducibility of the promoter were discovered (SEQ ID NO: 27). A myb-like factor (e.g., MYBYS) was found to activate the ChrC promoter sequence, deciphering another crucial component in this tightly regulated pathway. MYBYS were found to activate GUS expression under the ChrC promoter region.

Altogether, the present findings place the plant Fibrillin/CDSP34 pathway as a pivotal mechanism for conferring general stress resistance and biotic stress resistance in particular.

Thus, according to one aspect of the present invention there is provided a method of increasing tolerance of a plant to biotic stress.

The method according to this aspect of the present invention is effected by contacting the plant with at least one agent capable of upregulating Fibrillin/CDSP34 expression in the plant; and preferably growing the plant under a stress condition, thereby increasing tolerance of the plant to the biotic stress (do not understand this paragraph).

As used herein the term "plant" refers to any plant which may benefit from increased tolerance to stress conditions. A suitable plant for use in accordance with the method of the present invention can be any monocotyledonous or dicotyledonous plant including, but not limited to, maize, wheat, barely, rye, oat, rice, soybean, peanut, pea, lentil and alfalfa, cotton, rapeseed, canola, pepper, sunflower, potato, tobacco, tomato, eggplant, eucalyptus, a tree, an ornamental plant, a perennial grass and a forage crop. Other plants (e.g., moss, coniferous plants, algae) are listed in http://www.nationmaster.com/encyclopedia/Plantae, incorporated herein by reference.

As used herein the phrase "increasing tolerance" refers to increasing the ability of a plant to endure a biotic or an abiotic stress (or a combination of same) without suffering a substantial alteration in metabolism, growth, productivity and/or viability. Preferably, the plants of the present invention exhibit at least about 2% more, 5% more, 10% more, 20% more, 30% more, 40% more, 50% more, 60% more, 70% more, 80% more, 90% more or even higher tolerance to stress than non-transgenic plants or plants which have not been treated with the agents of the present invention as listed below.

As used herein the phrase "biotic stress" refers to an adverse effect on metabolism, growth (e.g., vigor, yield and/or biomass), reproduction and/or viability of a plant inflicted by a biotic entity. Examples of biotic stress conditions include, but are not limited to, nematode infection, oomycetal infection (e.g., Phytopthora) bacterial infection (e.g., Xanthomonas spp., Pseudomonas spp., Corynebacterium michiganense) phytoplasm, mycoplasmas, spiroplasms infection; fungal infection (e.g., Botrytis cinerea, Sphaerotheca fuliginea Fusarium spp. Thielaviopsis spp., Rhizoctonia spp, Alternaria solani, Septoria lycopersici, Colletotrichum spp, Oidiopsis spp), viral infection (e.g., TMV, PVY, TYLCV, tomato spotted wilt virus (TSWV), cucumber mosaic virus (CMV), parasitic plant infection (e.g., mistletoe, dodder), viroidal infection, and protozoan infection.

As used herein "an agent capable of upregulating Fibrillin/CDSP34 expression" refers to Fibrillin/CDSP34 per se as well as activators (i.e., molecules capable of activating Fibrillin/CDSP34 transcription or activity) and effectors thereof.

The agent of the present invention can be a nucleic acid sequence (polynucleotide), an amino acid sequence (polypeptide) and a chemical, as will be further described hereinbelow.

Assays for identifying additional agents and optimizing an agent or a combination of agents are well known in the art and may include, assaying transcriptional activation of Fibrillin/CDSP34 and assaying stress endurance of the plants (such as described in the Examples section which follows).

As used herein the term "Fibrillin/CDSP34" refers to endogenous or exogenous polynucleotides expressing the Fibrillin/CDSP34 (ChrC) gene expression product (polypeptide sequences) as well as homologs and variants of same (naturally occurring or synthetic) provided that functionality as maintained (i.e., increasing tolerance to stress, as described above). Preferably the Fibrillin/CDSP34 includes the conserved region identified in NCBI as pfam04755. Examples of Fibrillin/CDSP34 include, but are not limited to Cucumis sativus CHRC (GenBank Accession No. AAD05165, SEQ ID NO: 26) Citrus unshiu CitPAP (GenBank Accession No. spQ9ZWQ8), Lycopersicon esculentum LeCHRC (GenBank Accession No. gb|ABC42191.1, SEQ ID NO: 3), Arabidopsis thaliana fibrillin (GenBank Accession No. emb|CAB77870.1) Arabidopsis thaliana PAP2 (GenBank Accession No. ref|NP_193955.1), Arabidopsis thaliana fibrillin precursor-like (GenBank Accession No. AAM67287) Solanum tuberosum CDSP-34 (GenBank Accession No. emb|CAA75558.1), Capsicum annuum fibrillin (GenBank Accession No. CAA50750, SEQ ID NO: 25), Solanum demissum fibrillin, (GenBank Accession No. emb|CAA10372.1), Brassica rapa PAP2, (GenBank Accession No. gb|AAK57562.1), Brassica rapa PAP1 (GenBank Accession No. gb|AAK57564.1) Brassica rapa PAP3 (GenBank Accession No. gb|AAK57563.1), Nicotiana tabacum PAP (GenBank Accession No. emb|CAA75657.1), Coffea canephora fibrillin (GenBank Accession No. gb|ABA43902.1), Medicago truncatula PAP fibrillin (GenBank Accession No. gb|ABD32657.1), Brassica napus fibrillin (GenBank Accession No. gb|AAD03693.1), Oryza sativa PAP2 (GenBank Accession No. sp|Q6K439), Oryza sativa fibrillin-like protein (GenBank Accession No. AA072593), Oryza sativa PAP3 (GenBank Accession No. gb|AAP55143.1), Medicago truncatula PAP fibrillin (GenBank Accession No. gb|ABD32658.1), Elaeis guineensis fibrillin-like protein (GenBank Accession No. gb|AAP74338.1) Pisum sativum Plastoglobulin-1 (GenBank Accession No. Q9ZP40), Solanum lycopersicum PAP (GenBank Accession No. CAA75658) Nostoc sp. Fibrillin (GenBank Accession No. gb|AAD38023.1) Trichodesmium erythraeum PAP fibrillin (GenBank Accession No. gb|ABG53567.1).

According to one embodiment of this aspect of the present invention Fibrillin/CDSP34 comprise an amino acid sequence at least 70%, 80%, 85%, 90%, 95%, 96%, 97%, 98%, 99% or even 100% homologous or identical to SEQ ID NO: 2 or 3, respectively).

An isolated polynucleotide comprising a nucleic acid sequence encoding Fibrillin/CDSP34 (e.g., the above-described) is also contemplated herein.

Examples of Fibrillin/CDSP34 activators include, but are not limited to, MYBYS and gibberellins (GA). As shown in Example 3 of the Examples section which follows, the present inventor has found, for the first time, that MYBYS bind a regulatory sequence in the ChrC promoter and mediate transcriptional activation of the latter. Similar findings were found for GA.

As used herein the term "gibberellin" refers to a synthetic or naturally occurring form of the diterpenoiod acids that are synthesized by the terpenoid pathway in plastids and then modified in the endoplasmic reticulum and cytosol until they reach their biologically-active form (i.e., capable of inducing expression of Fibrillin/CDSP34). All gibberellins are derived from the ent-gibberellane skeleton, but are synthesized via ent-kauren. Any gibberellin may be used in accordance with the teachings of the present invention (e.g., GA1, GA2, GA3 ... GA136 and the like), though GA3 (Gibberellic acid) is preferred. Assaying for selecting a preferred GA for use in accordance with the present invention are described hereinabove.

As used herein the term "MYBYS" refers to an endogenous or exogenous polynucleotide (SEQ ID NO: 28) expressing the MYBYS gene expression product (polypeptide sequence, SEQ ID NO: 29). Also contemplated are homologous sequences of MYBYS e.g., at least about 70%, at least about 75%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 93%, at least about 94%, at least about 95%, at least about 96%, at least about 97%, at least about 98%, at least about 99%, or more say 100% homologous or identical to SEQ ID NO: 29 or 28 respectively.

While further reducing the present invention to practice the present inventor uncovered increased ChrC expression upon heat shock induction (see Example 1 of the Examples section which follows). These findings suggest that the aforementioned agents may be also used for increasing plant's tolerance to elevated temperatures.

As used herein the phrase "heat shock stress" refers to an adverse effect on metabolism, growth (e.g., vigor, yield and/or biomass), reproduction and/or viability of a plant inflicted by temperature conditions. A heat shock stress is plant specific.

As used herein, the term "exogenous polynucleotide" refers to a nucleic acid sequence which is not naturally expressed within the plant but which, when introduced into the plant either in a stable or transient manner, produces at least one polypeptide product.

Homology (e.g., percent homology) can be determined using any homology comparison software, including for example, the BlastP software of the National Center of Biotechnology Information (NCBI) such as by using default parameters.

Identity (e.g., percent homology) can be determined using any homology comparison software, including for example, the BlastN software of the National Center of Biotechnology Information (NCBI) such as by using default parameters.

The amino acid sequence encoded by the nucleic acid sequences of the present invention may comprise mutations, such as deletions, insertions or substitutions of one or more amino acids, either naturally occurring or man induced, either randomly or in a targeted fashion. Similarly, nucleic acid variations (e.g., deletions, insertions or substitutions of one or more amino acids, either naturally occurring or man induced, either randomly or in a targeted fashion) are also contemplated herein provided that functionality is maintained [e.g., conferring stress resistance to plants expressing same or promoter activity (constitutive or induced)].

As used herein the phrase "nucleic acid sequence" refers to a single or double stranded nucleic acid sequence which is isolated and provided in the form of an RNA sequence, a complementary nucleic acid sequence (cDNA), a genomic nucleic acid sequence and/or a composite nucleic acid sequences (e.g., a combination of the above).

As used herein the phrase "complementary nucleic acid sequence" refers to a sequence, which results from reverse transcription of messenger RNA using a reverse transcriptase or any other RNA dependent DNA polymerase. Such a sequence can be subsequently amplified in vivo or in vitro using a DNA dependent DNA polymerase.

As used herein the phrase "genomic nucleic acid sequence" refers to a sequence derived (isolated) from a chromosome and thus it represents a contiguous portion of a chromosome.

As used herein the phrase "composite nucleic acid sequence" refers to a sequence, which is at least partially complementary and at least partially genomic. A composite sequence can include some exonal sequences required to encode the polypeptide of the present invention, as well as some intronic sequences interposing therebetween. The intronic sequences can be of any source, including of other genes, and typically will include conserved splicing signal sequences. Such intronic sequences may further include cis acting expression regulatory elements.

Nucleic acid sequences of the polypeptides of the present invention may be optimized for expression. Examples of such sequence modifications include, but are not limited to, an altered G/C content to more closely approach that typically found in the plant species of interest, and the removal of codons atypically found in the plant species commonly referred to as codon optimization.

The phrase "codon optimization" refers to the selection of appropriate DNA nucleotides for use within a structural gene or fragment thereof that approaches codon usage within the plant of interest. Therefore, an optimized gene or nucleic acid sequence refers to a gene in which the nucleotide sequence of a native or naturally occurring gene has been modified in order to utilize statistically-preferred or statistically-favored codons within the plant. The nucleotide sequence typically is examined at the DNA level and the coding region optimized for expression in the plant species determined using any suitable procedure, for example as described in Sardana et al. (1996, Plant Cell Reports 15:677-681). In this method, the standard deviation of codon usage, a measure of codon usage bias, may be calculated by first finding the squared proportional deviation of usage of each codon of the native gene relative to that of highly expressed plant genes, followed by a calculation of the average squared deviation. The formula used is: $1 \text{ SDCU} = n=1 \text{ N}[(X_n-Y_n)/Y_n]2/N$, where $X_n$ refers to the frequency of usage of codon n in highly expressed plant genes, where $Y_n$ to the frequency of usage of codon n in the gene of interest and N refers to the total number of codons in the gene of interest. A table of codon usage from highly expressed genes of dicotyledonous plants is compiled using the data of Murray et al. (1989, Nuc Acids Res. 17:477-498).

One method of optimizing the nucleic acid sequence in accordance with the preferred codon usage for a particular plant cell type is based on the direct use, without performing any extra statistical calculations, of codon optimization tables such as those provided on-line at the Codon Usage Database through the NIAS (National Institute of Agrobiological Sciences) DNA bank in Japan (http://www.kazusa.orjp/codon/). The Codon Usage Database contains codon usage tables for a number of different species, with each codon usage table having been statistically determined based on the data present in Genbank By using the above mentioned information to determine the most preferred or most favored codons for each amino acid in a particular species (for example, rice), a naturally-occurring nucleotide sequence encoding a protein of interest can be codon optimized for that particular plant species. This is effected by replacing codons that may have a low statistical incidence in the particular species genome with corresponding codons, in regard to an amino acid, that are statistically more favored. However, one or more less-favored codons may be selected to delete existing restriction sites, to create new ones at potentially useful junctions (5' and 3' ends to add signal peptide or termination cassettes, internal sites that might be used to cut and splice segments together to produce a correct full-length sequence), or to eliminate nucleotide sequences that may negatively effect mRNA stability or expression.

The naturally-occurring encoding nucleotide sequence may already, in advance of any modification, contain a number of codons that correspond to a statistically-favored codon in a particular plant species. Therefore, codon optimization of the native nucleotide sequence may comprise determining which codons, within the native nucleotide sequence, are not statistically-favored with regards to a particular plant, and modifying these codons in accordance with a codon usage table of the particular plant to produce a codon optimized derivative. A modified nucleotide sequence may be fully or partially optimized for plant codon usage provided that the protein encoded by the modified nucleotide sequence is produced at a level higher than the protein encoded by the corresponding naturally occurring or native gene. Construction of synthetic genes by altering the codon usage is described in for example PCT Patent Application 93/07278.

Expressing the exogenous polynucleotides of the present invention within the plant can be effected by transforming one or more cells of the plant with the exogenous polynucleotide, followed by generating a mature plant (transgenic plant) from the transformed cells and cultivating the mature plant under conditions suitable for expressing the exogenous polynucleotide within the mature plant (e.g., induction of stress, GA treatment and expression of one or more additional exogenous polynucleotides).

Preferably, the transformation is effected by introducing to the plant cell a nucleic acid construct which includes the exogenous polynucleotide of the present invention and at least one promoter capable of directing transcription of the exogenous polynucleotide in the plant cell. Further details of suitable transformation approaches are provided hereinbelow.

As used herein, the term "promoter" refers to a region of DNA which lies upstream of the transcriptional initiation site of a gene to which RNA polymerase binds to initiate transcription of RNA. The promoter controls where (e.g., which portion of a plant, which organ within an animal, etc.) and/or when (e.g., which stage or condition in the lifetime of an organism) the gene is expressed.

Any suitable promoter sequence can be used in a nucleic acid construct used in accordance with the present invention. Preferably the promoter is a constitutive promoter, a tissue-specific, or an abiotic/biotic stress-inducible promoter.

Suitable constitutive promoters include, for example, CaMV 35S promoter (Odell et al., Nature 313:810-812, 1985); maize Ubi 1 (Christensen et al., Plant Sol. Biol. 18:675-689, 1992); rice actin (McElroy et al., Plant Cell 2:163-171, 1990); pEMU (Last et al., Theor. Appl. Genet. 81:581-588, 1991); and Synthetic Super MAS (Ni et al., The Plant Journal 7: 661-76, 1995). Other constitutive promoters include those in U.S. Pat. Nos. 5,659,026, 5,608,149; 5,608,144; 5,604,121; 5,569,597: 5,466,785; 5,399,680; 5,268,463; and 5,608,142. Preferably, the constitutive promoter is any part of the CHRC promoter (e.g., 1460 bp, SEQ ID NO: 31) which is modulated to have a constitutive promoter activity. Thus, such a promoter sequence may be of any length such as no more (or no longer than) than 20 bp, no more than 30 bp, no more than 50 bp, no more than 100 bp, no more than 200 bp, no more than 500 bp, no more than 700 bp, no more than 1000 bp or 1500 bp. Such a sequence may be deleted from a sequence of 18 bp from within this promoter (SEQ ID NO:32), characterized, as described in Example 3, to be the minimal sequence conferring an inducible activity Thus, constitutive promoters may be derived from deleting SEQ ID NO:32 from SEQ ID NOs 33, 6, 5 and 7 (SEQ ID NO: 8 or SEQ ID NO: 35). In addition, 3 nucleic acids were found to be critical for the inducible activity within the 18 bp sequence. Therefore, an additional constitutive promoter is any part of the CHRC promoter (1460 bp, SEQ ID NO: 31) which comprises SEQ ID NO: 32, which further comprises a mutated SEQ ID NO: 27. Methods for mutating a sequence are well known in the art, e.g., using PCR with a mutated primer, as described in Example 3. For example, constitutive promoters can be made with the primer set forth in SEQ ID NO: 21

Suitable tissue-specific promoters include, but not limited to, leaf-specific promoters such as described, for example, by Yamamoto et al., Plant J. 12:255-265, 1997; Kwon et al., Plant Physiol. 105:357-67, 1994; Yamamoto et al., Plant Cell Physiol. 35:773-778, 1994; Gotor et al., Plant J. 3:509-18, 1993; Orozco et al., Plant Mol. Biol. 23:1129-1138, 1993; and Matsuoka et al., Proc. Natl. Acad. Sci. USA 90:9586-9590, 1993.

Suitable abiotic stress-inducible promoters include, but not limited to, salt-inducible promoters such as RD29A (Yamaguchi-Shinozalei et al., Mol. Gen. Genet. 236:331-340, 1993); drought-inducible promoters such as maize rab17 gene promoter (Pla et. al., Plant Mol. Biol. 21:259-266, 1993), maize rab28 gene promoter (Busk et. al., Plant J. 11:1285-1295, 1997) and maize Ivr2 gene promoter (Pelleschi et. al., Plant Mol. Biol. 39:373-380, 1999); and heat-inducible promoters such as heat tomato hsp80-promoter from tomato (U.S. Pat. No. 5,187,267).

According to a preferred embodiment of the present invention an inducible ChrC promoter sequence is used which comprises the 18 bp sequence element coferring inducible properties to the ChrC promoter (SEQ ID NO: 32), in which, as described hereinabove, SEQ ID NO: 27, is preferably not mutated. These include for example, SEQ ID NOs: 33, 32, 31, 6, 5 and 7, and, in addition, promoter sequences as SEQ ID NOs: 33, 32, 31, 6, 5 and 7, comprising one of SEQ ID NOs 22, 23, and 24.

It is to be understood that the present findings suggest the use of the ChrC inducible promoter for driving expression of any heterologous gene of interest in a GA regulated manner.

Thus, the present invention further provides a method of inducing expression of an exogenous gene of interest in a plant. The method comprising transforming the plant with a nucleic acid construct comprising a nucleic acid sequence encoding the gene of interest, the nucleic acid sequence being operably linked to SEQ ID NO: 32, to thereby obtain a transgenic plant; and subjecting said transgenic plant to gibberellin (GA), thereby inducing the expression of the gene of interest in the plant.

Nucleic acid constructs of the present invention preferably further include an appropriate selectable marker and/or an origin of replication. Preferably, the nucleic acid construct utilized is a shuttle vector, which can propagate both in E. coli (wherein the construct comprises an appropriate selectable marker and origin of replication) and be compatible with propagation in cells. The construct according to the present invention can be, for example, a plasmid, a bacmid, a phagemid, a cosmid, a phage, a virus or an artificial chromosome.

The nucleic acid construct of the present invention can be utilized to stably or transiently transform plant cells. In stable transformation, the exogenous polynucleotide of the present invention is integrated into the plant genome and as such it represents a stable and inherited trait. In transient transformation, the exogenous polynucleotide is expressed by the cell transformed but it is not integrated into the genome and as such it represents a transient trait.

There are various methods of introducing foreign genes into both monocotyledonous and dicotyledonous plants (Potrykus, I., Annu. Rev. Plant. Physiol., Plant. Mol. Biol. (1991) 42:205-225; Shimamoto et al., Nature (1989) 338:274-276).

The principle methods of causing stable integration of exogenous DNA into plant genomic DNA include two main approaches:

(i) *Agrobacterium*-mediated gene transfer: Klee et al. (1987) Annu. Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S. and Arntzen, C. J., Butterworth Publishers, Boston, Mass. (1989) p. 93-112.

(ii) Direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217; glass fibers or silicon carbide whisker transformation of cell cultures, embryos or callus tissue, U.S. Pat. No. 5,464,765 or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

The *Agrobacterium* system includes the use of plasmid vectors that contain defined DNA segments that integrate into the plant genomic DNA. Methods of inoculation of the plant tissue vary depending upon the plant species and the *Agrobacterium* delivery system. A widely used approach is the leaf disc procedure which can be performed with any tissue explant that provides a good source for initiation of whole plant differentiation. Horsch et al. in Plant Molecular Biology Manual A5, Kluwer Academic Publishers, Dordrecht (1988) p. 1-9. A supplementary approach employs the *Agrobacterium* delivery system in combination with vacuum infiltration. The *Agrobacterium* system is especially viable in the creation of transgenic dicotyledonous plants.

There are various methods of direct DNA transfer into plant cells. In electroporation, the protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals or tungsten particles, and the microprojectiles are physically accelerated into cells or plant tissues.

Following stable transformation plant propagation is exercised. The most common method of plant propagation is by seed. Regeneration by seed propagation, however, has the deficiency that due to heterozygosity there is a lack of uniformity in the crop, since seeds are produced by plants according to the genetic variances governed by Mendelian rules. Basically, each seed is genetically different and each will grow with its own specific traits. Therefore, it is preferred that the transformed plant be produced such that the regenerated plant has the identical traits and characteristics of the parent transgenic plant. Therefore, it is preferred that the transformed plant be regenerated by micropropagation which provides a rapid, consistent reproduction of the transformed plants.

Micropropagation is a process of growing new generation plants from a single piece of tissue that has been excised from a selected parent plant or cultivar. This process permits the mass reproduction of plants having the preferred tissue expressing the fusion protein. The new generation plants which are produced are genetically identical to, and have all of the characteristics of, the original plant. Micropropagation allows mass production of quality plant material in a short period of time and offers a rapid multiplication of selected cultivars in the preservation of the characteristics of the original transgenic or transformed plant. The advantages of cloning plants are the speed of plant multiplication and the quality and uniformity of plants produced.

Micropropagation is a multi-stage procedure that requires alteration of culture medium or growth conditions between stages. Thus, the micropropagation process involves four basic stages: Stage one, initial tissue culturing; stage two, tissue culture multiplication; stage three, differentiation and plant formation; and stage four, greenhouse culturing and hardening. During stage one, initial tissue culturing, the tissue culture is established and certified contaminant-free. During stage two, the initial tissue culture is multiplied until a sufficient number of tissue samples are produced to meet production goals. During stage three, the tissue samples grown in stage two are divided and grown into individual plantlets. At stage four, the transformed plantlets are transferred to a greenhouse for hardening where the plants' tolerance to light is gradually increased so that it can be grown in the natural environment.

Although stable transformation is presently preferred, transient transformation of leaf cells, meristematic cells or the whole plant is also envisaged by the present invention.

Transient transformation can be effected by any of the direct DNA transfer methods described above or by viral infection using modified plant viruses.

Viruses that have been shown to be useful for the transformation of plant hosts include CaMV, TMV and BV. Transformation of plants using plant viruses is described in U.S. Pat. No. 4,855,237 (BGV), EP-A 67,553 (TMV), Japanese Published Application No. 63-14693 (TMV), EPA 194,809 (BV), EPA 278,667 (BV); and Gluzman, Y. et al., Communications in Molecular Biology: Viral Vectors, Cold Spring Harbor Laboratory, New York, pp. 172-189 (1988). Pseudovirus particles for use in expressing foreign DNA in many hosts, including plants, is described in WO 87/06261.

Preferably, the virus of the present invention is avirulent and thus is incapable of causing severe symptoms such as reduced growth rate, mosaic, ring spots, leaf roll, yellowing, streaking, pox formation, tumor formation and pitting. A suitable avirulent virus may be a naturally occurring avirulent virus or an artificially attenuated virus. Virus attenuation may be effected by using methods well known in the art including, but not limited to, sub-lethal heating, chemical treatment or by directed mutagenesis techniques such as described, for example, by Kurihara and Watanabe (Molecular Plant Pathology 4:259-269, 2003), Gal-on et al. (1992), Atreya et al. (1992) and Huet et al. (1994).

Suitable virus strains can be obtained from available sources such as, for example, the American Type culture Collection (ATCC) or by isolation from infected plants. Isolation of viruses from infected plant tissues can be effected by techniques well known in the art such as described, for example by Foster and Tatlor, Eds. "Plant Virology Protocols From Virus Isolation to Transgenic Resistance (Methods in Molecular Biology (Humana Pr), Vol 81)", Humana Press, 1998. Briefly, tissues of an infected plant believed to contain a high concentration of a suitable virus, preferably young leaves and flower petals, are ground in a buffer solution (e.g., phosphate buffer solution) to produce a virus infected sap which can be used in subsequent inoculations.

Construction of plant RNA viruses for the introduction and expression of non-viral exogenous polynucleotide sequences in plants is demonstrated by the above references as well as by Dawson, W. O. et al., Virology (1989) 172:285-292; Takamatsu et al. EMBO J. (1987) 6:307-311; French et al. Science (1986) 231:1294-1297; and Takamatsu et al. FEBS Letters (1990) 269:73-76.

When the virus is a DNA virus, suitable modifications can be made to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria. Transcription and translation of this DNA will produce the coat protein which will encapsidate the viral DNA. If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

Construction of plant RNA viruses for the introduction and expression in plants of non-viral exogenous polynucleotide sequences such as those included in the construct of the present invention is demonstrated by the above references as well as in U.S. Pat. No. 5,316,931.

In one embodiment, a plant viral polynucleotide is provided in which the native coat protein coding sequence has been deleted from a viral polynucleotide, a non-native plant viral coat protein coding sequence and a non-native promoter, preferably the subgenomic promoter of the non-native coat protein coding sequence, capable of expression in the plant host, packaging of the recombinant plant viral polynucleotide, and ensuring a systemic infection of the host by the recombinant plant viral polynucleotide, has been inserted. Alternatively, the coat protein gene may be inactivated by insertion of the non-native polynucleotide sequence within it, such that a protein is produced. The recombinant plant viral polynucleotide may contain one or more additional non-native subgenomic promoters. Each non-native subgenomic promoter is capable of transcribing or expressing adjacent genes or polynucleotide sequences in the plant host and incapable of recombination with each other and with native subgenomic promoters. Non-native (foreign) polynucleotide sequences may be inserted adjacent the native plant viral subgenomic promoter or the native and a non-native plant viral subgenomic promoters if more than one polynucleotide sequence is included. The non-native polynucleotide sequences are transcribed or expressed in the host plant under control of the subgenomic promoter to produce the desired products.

In a second embodiment, a recombinant plant viral polynucleotide is provided as in the first embodiment except that the native coat protein coding sequence is placed adjacent one of the non-native coat protein subgenomic promoters instead of a non-native coat protein coding sequence.

In a third embodiment, a recombinant plant viral polynucleotide is provided in which the native coat protein gene is adjacent its subgenomic promoter and one or more non-native subgenomic promoters have been inserted into the viral polynucleotide. The inserted non-native subgenomic promoters are capable of transcribing or expressing adjacent genes in a plant host and are incapable of recombination with each other and with native subgenomic promoters. Non-native polynucleotide sequences may be inserted adjacent the non-native subgenomic plant viral promoters such that the sequences are transcribed or expressed in the host plant under control of the subgenomic promoters to produce the desired product.

In a fourth embodiment, a recombinant plant viral polynucleotide is provided as in the third embodiment except that the native coat protein coding sequence is replaced by a non-native coat protein coding sequence.

The viral vectors are encapsidated by the coat proteins encoded by the recombinant plant viral polynucleotide to produce a recombinant plant virus. The recombinant plant viral polynucleotide or recombinant plant virus is used to infect appropriate host plants. The recombinant plant viral polynucleotide is capable of replication in the host, systemic spread in the host, and transcription or expression of foreign gene(s) (exogenous polynucleotide) in the host to produce the desired protein.

Techniques for inoculation of viruses to plants may be found in Foster and Taylor, eds. "Plant Virology Protocols: From Virus Isolation to Transgenic Resistance (Methods in Molecular Biology (Humana Pr), Vol 81)", Humana Press, 1998; Maramorosh and Koprowski, eds. "Methods in Virology" 7 vols, Academic Press, New York 1967-1984; Hill, S. A. "Methods in Plant Virology", Blackwell, Oxford, 1984; Walkey, D. G. A. "Applied Plant Virology", Wiley, New York, 1985; and Kado and Agrawa, eds. "Principles and Techniques in Plant Virology", Van Nostrand-Reinhold, New York.

In addition to the above, the polynucleotide of the present invention can also be introduced into a chloroplast genome thereby enabling chloroplast expression.

A technique for introducing exogenous polynucleotide sequences to the genome of the chloroplasts is known. This technique involves the following procedures. First, plant cells are chemically treated so as to reduce the number of chloroplasts per cell to about one. Then, the exogenous polynucleotide is introduced via particle bombardment into the cells with the aim of introducing at least one exogenous polynucleotide molecule into the chloroplasts. The exogenous polynucleotides selected such that it is integratable into the chloroplast's genome via homologous recombination which is readily effected by enzymes inherent to the chloroplast. To this end, the exogenous polynucleotide includes, in addition to a gene of interest, at least one polynucleotide stretch which is derived from the chloroplast's genome. In addition, the exogenous polynucleotide includes a selectable marker, which serves by sequential selection procedures to ascertain that all or substantially all of the copies of the chloroplast genomes following such selection will include the exogenous polynucleotide. Further details relating to this technique are found in U.S. Pat. Nos. 4,945,050; and 5,693,507 which are incorporated herein by reference. A polypeptide can thus be produced by the protein expression system of the chloroplast and become integrated into the chloroplast's inner membrane.

Since a number of genes in the fibrillin/CDSP34 pathway may confer resistance to stress, the present invention also envisages expressing a plurality of exogenous polynucleotides in a single host plant to thereby achieve superior stress tolerance.

Expressing a plurality of exogenous polynucleotides in a single host plant can be effected by co-introducing multiple nucleic acid constructs, each including a different exogenous polynucleotide, into a single plant cell. The transformed cell can than be regenerated into a mature plant using the methods described hereinabove.

Alternatively, expressing a plurality of exogenous polynucleotides in a single host plant can be effected by co-introducing into a single plant-cell a single nucleic-acid construct including a plurality of different exogenous polynucleotides. Such a construct can be designed with a single promoter sequence which can transcribe a polycistronic message including all the different exogenous polynucleotide sequences. To enable co-translation of the different polypeptides encoded by the polycistronic message, the polynucleotide sequences can be inter-linked via an internal ribosome entry site (IRES) sequence which facilitates translation of polynucleotide sequences positioned downstream of the IRES sequence. In this case, a transcribed polycistronic RNA molecule encoding the different polypeptides described above will be translated from both the capped 5' end and the two internal IRES sequences of the polycistronic RNA molecule to thereby produce in the cell all different polypeptides. Alternatively, the construct can include several promoter sequences each linked to a different exogenous polynucleotide sequence.

The plant cell transformed with the construct including a plurality of different exogenous polynucleotides, can be regenerated into a mature plant, using the methods described hereinabove.

Alternatively, expressing a plurality of exogenous polynucleotides in a single host plant can be effected by introducing different nucleic acid constructs, including different exogenous polynucleotides, into a plurality of plants. The regenerated transformed plants can then be cross-bred and resultant progeny selected for superior abiotic stress tolerance and/or biomass traits, using conventional plant breeding techniques.

Preferably, mature transformed plants generated as described above are further selected for stress tolerance. Accordingly, transformed and non-transformed (as well as GA treated and non treated plants, wild type) plants are exposed to a biotic or abiotic stress condition of interest such as pathogen infection, water depravation, suboptimal temperature (e.g., elevated temperature as compared to the plants optimal temperature growth conditions), nutrient deficiency, or a salt stress condition. Since different plants vary considerably in their tolerance to a specific stress, the growth condition is preferably adjusted according to the specific characteristics of the specific plant cultivar or variety, so as to inflict a mild or moderate effect on the physiology and/or morphology of the plants (for guidelines as to appropriate concentration please see, Bernstein and Kafkafi, Root Growth Under Salinity Stress In: Plant Roots, The Hidden Half 3rd ed. Waisel Y, Eshel A and Kafkafi U. (editors) Marcel Dekker Inc., New York, 2002, and reference therein). Following exposure to the stress condition the plants are frequently monitored until substantial physiological and/or morphological effects appear in wild type plants. Subsequently, transformed plants not exhibiting substantial physiological and/or morphological effects, or exhibiting higher biomass than wild-type plants, are identified as abiotic stress tolerant plants.

As used herein the phrase "abiotic stress" refers to any adverse effect on metabolism, growth, reproduction and/or viability of a plant. Accordingly, abiotic stress can be induced by suboptimal environmental growth conditions such as, for example, drought, water deprivation, flood, high temperature, low temperature, oxidative stress, aging, heavy metal toxicity, wound, light, anaerobiosis, damaging chemicals, nutrient deficiency, nutrient excess, atmospheric pollution and irradiation salinity, flooding, freezing, heavy metal toxicity, atmospheric pollution or UV irradiation and herbicidal exposure.

The phrase "abiotic stress tolerance" as used herein refers to the ability of a plant to endure an abiotic stress without suffering a substantial alteration in metabolism, growth, productivity and/or viability. Preferably, the plants of the present invention exhibit at least about 2% more, 5% more, 10% more, 20% more, 30% more, 40% more, 50% more, 60% more, 70% more, 80% more, 90% more or even higher tolerance to abiotic stress than non-SEQ ID NO: 3 expressing plants.

It will be appreciated that plants of the present invention grown under stress are envisioned to exhibit superior phenotype when grown in suboptimal conditions. Moreover, tolerance to abiotic stress enables growing the plants of the present invention under abiotic stress conditions which give an additional advantage for enduring biotic stress.

Thus, under a preferred embodiment, the plants of the present invention are grown under biotic or abiotic stress conditions such as drought or heat stress.

The biotic or abiotic stress conditions can be naturally induced in the environment in which the plant is grown, or can be intentionally inflicted as part of the cultivation plan. For example, low temperature or heat shock conditions can be induced by growing the plants of the present invention in a temperature controlled green house. Salt stress can be effected in many ways such as, for example, by irrigating the plants with a hyperosmotic solution, by cultivating the plants hydroponically in a hyperosmotic growth solution (e.g., Hoagland solution), or by culturing the plants in a hyperosmotic growth medium (e.g., MS medium).

The plants of the present invention can additionally be exposed to other treatments for enduring various stress conditions and improving plants performance. Treatments against biotic stress can include for example pesticides or use of barriers e.g. nets or nylon. Treatments against abiotic stress conditions can include for example heating, cooling, irrigation, windbreaking and the like.

Hence, the present application provides methods of utilizing novel abiotic stress-tolerance agents to increase tolerance to stress (biotic/abiotic) and/or biomass in a wide range of economical plants, in a safe and cost effective manner.

Agents of the present invention are expected to increase the overall biomass, vigor and/or yield of the plant under stress.

As used herein the phrase "plant biomass" refers to the amount or quantity of tissue produced from the plant in a growing season, which could also determine or affect the plant yield or the yield per growing area.

As used herein the phrase "plant vigor" refers to the amount or quantity of tissue produced from the plant in a given time. Hence increase vigor could determine or affect the plant yield or the yield per growing time or growing area.

As used herein the phrase "plant yield" refers to the amount or quantity of tissue produced and harvested as the plant produced product. Hence increase yield could affect the economic benefit one can obtain from the plant in a certain growing are and/or growing time.

Preferably, the (e.g., genetically engineered) plants of the present invention exhibit at least about 2% more, 5% more, 10% more, 20% more, 30% more, 40% more, 50% more, 60% more, 70% more, 80% more, 90% more or even greater biomass, vigor and/or yield than non-transgenic plants.

Methods of assaying plant vigor, yield and biomass are well known in the art.

Thus, the present invention is of high agricultural value for promoting the yield of commercially desired crops coniferous plants (moss, algae, monocot or dicot, as well as other plants listed in http://www.nationmaster.com/encyclopedia/Plantae) under stress conditions As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Analysis of Expression of ChrC and the Tomato Homolog LeChrC

The tomato homolog of the cucumber ChrC was cloned and sequenced. Both homologs showed elevation of expression under pathogen or heat stress, as depicted by RNA-blot and GUS expression assays.

Materials and Experimental Procedures

Plant material and definition of developmental stages—Cucumber (*Cucumis sativus* L. cv Shimshon) and tomato (*Lycopersicon esculentum* Mill. cv Adi) plants were grown under standard greenhouse conditions as previously described (Vishnevetsky et al., Plant J. 20, 423-431, 1999).

Cloning of the tomato ChrC homolog, LeChrC—ChrC, a cucumber (*C. sativus*) plastid lipid-associated protein (PAP), has been suggested to be transcriptionally activated in carotenoid-accumulating flowers by gibberellin (GA). Based on the tomato EST database (http://compbio.dfci.harvard.edu/tgi/tgipage.html), the tomato (*L. esculentum*) ChrC homologue was identified and cloned (LeChrC, 775 bp; SEQ ID NO: 1) into pBluescript IISK from a tomato petal cDNA library (Chmelnitsky I, Sobolev I, Barg R, Shabtai S, Salts Y *Euphytica* 129:229-236, 2003), using two primers: forward F47 (5'-TGCTCTTTCTCTGTTTCACTCTGA-3'; SEQ ID NO: 10) and reverse R822 (5'-TTGTCCCAA-GAAT-TCAACGTTC-3'; SEQ ID NO: 11).

Database search—BLAST search was effected for the amino acid sequence of LeChrC in The Institute for Genomic Research (TIGR) database (http://www.tigr.org/).

Sequence analysis of LeChrC—Multiple sequence alignment of amino-acid sequences was effected with CLUSTAL W (Thompson et al., Nucl. Acid. Res. 22, 4673-4680, 1994). Sequences aligned were of *L. esculentum* LeChrC (GenBank Accession No. DQ310151, SEQ ID NO: 3), *Capsicum annuum* Fib (GenBank Accession No. CAA50750; SEQ ID NO: 25) and *C. sativus* ChrC (GenBank Accession No. AAD05165; SEQ ID NO: 26).

Expression analysis—Total RNA, was extracted, as described previously (Vishnevetsky et al., Plant J. 10, 1111-

1118, 1996), from cucumber or tomato leaves and corollas at different developmental stages (stages 1-4 as described in Table 1 below). Thereafter, 10 µg of total RNA was fractionated through a 1.6% formaldehyde gel and transferred to a Hybond-N+ filter (Amersham Biosciences, Buckinghamshire, UK). Specific probing were effected by labeling of ChrC and LeChrC cDNA clones with $^{32}$P using a random priming kit (Rediprime, Amersham Biosciences). A probe for rRNA was used as a control. The blots were hybridized at 60° C. as described in Vishnevetsky et al (Plant J. 10, 1111-1118, 1996) and the membranes were washed twice in 2×SSC, 0.1% (w/v) SDS at 60° C. for 20 min each and exposed to X-ray film (Fuji, Tokyo, Japan) at −70° C. Determining temporal and spatial expression of LeChrC was preformed on RNA extracted from different tomato tissues (leaves, petals and flower parts), at different developmental stages (1-3, as described in Table 1 below).

TABLE 1

|  | stages | Hours before anethesis |
|---|---|---|
| Cucumber | 1 | 120 |
|  | 2 | 72 |
|  | 3 | 24 |
|  | 4 | 0 (anethesis) |
| Tomato | 1 | 84 |
|  | 2 | 48 |
|  | 3 | 12 |
|  | 4 | 0 (anthesis) |

ChrC:GUS transient-expression assay—Plants or leaves were bombarded with the ChrC:GUS construct, generated as previously described (pGEM3Z/201.2; Vishnevetsky et al., Plant J. 20, 423-431, 1999), containing 3,500 bp of the ChrC promoter (5'UTR of the ChrC gene) located upstream of the GUS gene (GenBank Accession No, AF502128). Bombardment was effected with Biolistic PDS 1000/He system (Bio-Rad, Hercules, Calif.) at a pressure of 1,350 dpi, as described by Vishnevetsky et al. (Plant J. 20, 423-431, 1999). Following bombardment, tissue was incubated for a few hours at 37° C. in a 0.1% (w/v) X-Gluc solution (5-bromo-4-chloro-3-indolyl b-D-GlcUA; Duchefa, Haarlem, The Netherlands) containing 0.1 M sodium phosphate buffer, pH 7.0, 10 mM EDTA, and 0.1% (w/v) Triton X-100.

Plant infection with *Botrytis*—*Botrytis cinerea* (isolate Bcl16, Guetsky et al., Biocontrol Sci. Technol. 12, 625-630, 2002) was maintained and grown for infection experiments on potato dextrose agar (PDA). Harvesting of conidia from the cultures was effected by agitating small pieces of 14-day-old agar bearing mycelium and conidia in a glass tube containing 2 ml tap water and 0.01% (w/v) Tween-80. The suspension was then filtered through a double layer of cheesecloth to screen out mycelium plugs and the conidial concentration was calibrated by hemacytometer, and adjusted to $5\times10^5$ cells/ml. Glucose (0.05%, w/v) and $KH_2PO_4$ (0.05%) were added to the conidial suspension. Infection of whole 1-month-old tomato plants was effected by placing 20 µl of the conidial suspension on four leaflets of each of four leaves on six plant replicates, and covering the plants with a polyethylene bag. Leaves were analyzed 3 days after inoculation.

Heat shock induction—Induction of heat shock was effected by culturing leaves in vitro for 4 hours at 42° C. Control leaves were cultured under the same conditions at room temperature.

Plant infection with powdery mildew—Infection of plants with powdery mildew [*Sphaerotheca fuliginea* (*Oidium* sp.)] was effected by inoculating the center of leaves with 10 µl of water containing 300-500 conidia of *S. fuliginea*.

Plant infection with viruses—Mechanical infection of plants was performed as previously described (*Natural Resistance Mechanisms of Plants to Viruses*, G. Lobenstein and J. P. Carr, Eds. Springer Verlag, 2006). Plants were infected with TYLCV, PVY and TMV.

TYLCV—Israeli strain, was collected from infected plants in the field in the 60's by Shlomo Cohen (Cohen, S. and Harpaz, I. Periodic rather than continual acquisition of a new tomato virus by its vector, the tobacco whitefly (*Bemisia Tabaci* Gennadius). Ent. Exp. and Appl. 7, 155-166, 1964).

PVY—Tomato necrotic strain, collected from the Besor region in the late 70's (Rosner, A., Lachman, A., Pearlsman, M., Maslenin, L. and Antignus, Y. Molecular characterization and differential diagnosis of a necrotic PVY isolate in tomato. Ann. Appl. Biol. 137: 253-257, 2000).

TMV—Tomato strain, Tomato Mosaic virus (ToMV) collected from infected plants in the field (Pilowsky, M., Frankel, R. and Cohen, S. Studies of the variable reaction at high temperature of F1 hybrid tomato plants resistant to tobacco mosaic virus. Phytopathology 71, 319-323, 1981).

Leaves were taken from plants three days, a week and two weeks after inoculation. Control treatments included leaves from plants that were mock-inoculated, and leaves that were taken prior to infection (L).

Results

The LeChrC sequence—The complete cDNA sequence of LeChrC (SEQ ID NO. 2; GenBank Accession No. DQ310151) was cloned and sequenced. As shown in the alignment presented in FIG. 1, the LeChrC amino acid sequence (SEQ ID NO. 3) shows homology to pepper Fib (SEQ ID NO: 25) and cucumber ChrC (SEQ ID NO: 26). The ChrC transit peptide, including 58 amino acids, which directs the ChrC protein to the plastid is underlined. The cleavage point of the precursor protein was determined based on the N-terminal microsequence of the mature ChrC (Vishnevetsky et al., The Plant Journal, 10, 1111-1118, 1996). LeChrC BLAST search in The Institute for Genomic Research (TIGR) database revealed the LeChrC sequence (TIGR Accession No. TC161992), and an additional tomato homolog (TIGR Accession No. TC162898), putatively coding for PAP with 37% identity at the amino acid level to LeChrC. Blast search of TIGR with a 5' partial sequence of LeChrC, did not reveal this second TC162898, thus conclusions can safely be made on the expression of LeChrC using analyses based on probes aimed at the LeChrC 5' sequence. The LeChrC was found to be 95.7% identical in amino acids to pepper Fib.

LeChrC expression—Analysis of LeChrC expression at the RNA level, as presented in FIG. 2, revealed spatial and temporal regulation which mimics that of ChrC in cucumber flowers and leaves, showing LeChrC is expressed in flower petals and essential parts in the later stages of development (stages 2 and 3). LeChrC RNA expression was not detected in leaves.

ChrC and LeChrC show induced expression under stress conditions—In a ChrC:GUS transient-expression assay, as shown in FIGS. 3*a*-*b*, ChrC expression was induced in heat-shock-treated (FIG. 3*a*) as well as pathogen (powdery mildew) infected (FIG. 3*b*) cucumber leaves. No GUS expression was detected at control, room-temperature-treated or uninfected leaves. Moreover, heat-shock-treated and powdery mildew-infected, stressed leaves showed higher levels of the ChrC transcript, as depicted by RNA-blot. (FIG. 3*c*).

FIGS. 4*a*-*b* further show that like ChrC, LeChrC transcript levels were higher following heat shock treatment and were further elevated following inoculation of tomato plants with viruses (TMV, PVY, TYLCV) and a fungus (*Botrytis cinerea*). Thus, stress induction, whether physical or due to pathogen invasion, leads to elevation of ChrC and LeChrC, (FIGS. 3 and 4) as evidenced by the GUS and RNA blot experiments.

Example 2

Tomatoes with RNAi-Suppressed LeChrC Showed Reduced Resistance to *Botrytis cinerea* Infection Creating an RNAi construct of LeChrC—A 530-bp fragment of the 5' area of LeChrC (nucleotides 35-565 of SEQ ID NO: 2; SEQ ID NO: 4) was generated by PCR using forward primer 5'-ATGGCTTCCATCTCTTCTCTCA-3' (SEQ ID NO: 12) and R2 reverse primer 5'-TCGAACCAGAAGCA-GATTGC-3' (SEQ ID NO: 13). The amplified fragment was then inserted into the pRNA69 plasmid (which allows expression of sequences as an inverted repeat, as described in Waterhouse et al., (Proc. Natl. Acad. Sci. USA 95, 13959-13964, 1998), 3' to the CaMV 35S promotor in an antisense and sense orientation, before and after the intron, respectively. The expression of the stem-loop-stem structure thus leads to suppression of endogenous homologue (Brodersena and Voinnet Trends in Genetics 22, 268-280, 2006). The resultant plasmid was digested with NotI, and the fragment was inserted into the binary vector pART27 (Gleave, Plant Mol. Biol. 20, 1203-1207, 1992).

ChrC over expressing transgenic tomatoes—Tomato transgenic lines that overaccumulate ChrC were generated and characterized by Vishnevetsky et al. (Plant J. 20, 423-431, 1999).

Evaluation of LeChrC suppression in tomato plants transformed with LeChrC RNAi—The RNAi construct described above was electroporated into the *Agrobacterium tumefaciens* strain AGLO and used for transformation of tomato as previously described (Vishnevetsky et al., Plant J. 20, 423-431, 1999). Following selection of transformed plants by kanamycin resistance, the regenerated plants were screened by PCR, using primers 35SF: 5'-CTATCCTTCGCAAGAC-CCTTCC-3' and R2:5'-TCGAACCAGAAGCAGATTGC-3. (SEQ ID NOs: 20 and 13, respectively), and characterized using RNA-blot expression analysis, effected as described in Example 1, to evaluate suppression of LeChrC.

*Botrytis* infection assay—*Botrytis cinerea* was maintained and grown for infection experiments as described in Example 1. Infection with *B. cinerea* was effected on whole plants (leaves and stems) or detached leaves of LeChrC RNAi suppressed transgenic plants (lines 11, 13, 37, effected as described above), a transgenic LeChrC overexpressing plant (sense) and control non-transgenic plants (WT). Infection of detached leaves was effected by placing 8-20 µl drops of the *B. cinerea* conidial suspension described in Example 1, on each of six leaves from each plant line. The leaves were then placed on a plastic grid laid over moist paper, and were then all placed in a box covered with transparent polyethylene to ensure high humidity. Infection of whole 1-month-old tomato plants was effected by placing 20 µl of the conidial suspension on four leaflets of each of four leaves on six plant replicates, and covering the plants with a polyethylene bag. Care was taken to avoid contact between the polyethylene and the inoculum drop. Stem infection was effected by placing on the stem surface, between the second and third node, 5-mm diameter mycelial discs that originated from the edge of a 4-day-old PDA culture of *B. cinerea*. Leaves and plants were incubated in a walk-in growth chamber set at 20±2° C. and a 12-h photoperiod. Disease severity on leaves in all experiments was determined as previously described (Guetsky et al., Biocontrol Sci. Technol. 12, 625-630, 2002), by estimating the size of the necrotic area developed from each suspension drop on a scale of 0-100%, where 100% severity is a lesion of 20 $mm^2$. Severity of stem infection was evaluated by measuring the length of the lesion. Disease severity was measured 3, 6 or 8 days following inoculation.

Expression analysis—Expression analysis of LeChrC was effected with RNA-blot as described in Example 1. Expression analysis of LeChRC was further effected with RT-PCR. Tomato total RNA was treated with RNase-free DNase and transcribed using oligo$(dT)_{15}$ primer and M-MLV Reverse Transcriptase (all reagents by Promega, Palo Alto, Calif.; procedures were effected according to the manufacturer's protocols). PCR amplifications for detection of LeChrC in the cDNA were effected with primers F47 and R822 (SEQ ID NOs: 10 and 11, respectively). Additionally, the expression of the control gene actin was determined using forward primer: 5'-GGTTTTGCTGGGGATGC-3' (SEQ ID NO: 14) and reverse primer: 5'-CATTGAATGTCTCAAACAG-TATTTGAGTC-3' (SEQ ID NO: 15).

Western blot analysis—Proteins were extracted from stage 3 tomato corollas, fractionated by 12.5% SDS-PAGE (50 mg per lane), and analyzed following western blotting using affinity-purified polyclonal antibodies against ChrC (Smirra et al, Plant Physiol. 102:491-496, 1993), and a chemiluminescence detection kit (Amersham Biosciences, Uppsia, Sweden; Vishnevetsky et al., Plant J. 20, 423-431, 1999). Prior to incubation with antibodies, membranes were stained with Ponceau-S red (Sigma-Aldrich, St. Lewis, Mo.) to evaluate equal protein loading amounts. Following incubation with antibodies, membranes were exposed to x-ray film (Fuji, Tokyo, Japan).

Analysis of protein content—Protein content was determined using a detergent-compatible protein assay (Bio-Rad, Hercules, Calif.).

Results

LeChrC RNAi transformed tomatoes showed suppression of LeChrC—Following transformation with LeChrC RNAi, RNA-blot analysis was effected to evaluate suppression of LeChrC. FIG. 5a shows that specific lines exhibited LeChrC suppression (lines 11, 13, 21, 28, 33, 37), thus confirming transformation and RNA inhibition of LeChrC, while other transgenic lines showed no suppression of LeChrC (lines 2, 19, 25). This is in conformity with the predictability of the siRNA gene silencing method (i.e., over 50%). The suppression of LeChrC in T2 generation plants was further confirmed in the LeChrC suppressed transgenic lines using RNA-blot with probes for LeChrC (FIG. 5b) and western-blot analyses with antisera against ChrC (FIG. 5c).

Tomatoes with RNAi-suppressed LeChrC showed reduced resistance to *Botrytis cinerea* infection—To evaluate the susceptibility of LeChrC-suppressed plants to *B. cinerea* infection, leaves were detached from these, and from control non-transgenic plants, and inoculated with *B. cinerea* conidia. Disease severity in leaves of plants with suppressed LeChrC expression, as presented in Table 2 below, was two- to three-fold higher than that in control plants (i.e., expressing unmodified levels of endogenous LeChrC). To further evaluate this susceptibility, a conidial suspension was applied to leaves and stems of 1-month-old plants and inoculated plants were then grown in a growth chamber. Three days after inoculation, there was no significant difference in the size of the necrotic lesions on leaves of transgenic LeChrC-suppressed vs. control plants. However, during the following 3 days of growth, as is shown in Table 3 below, and in FIGS. 6a-c, lesions on the RNAi transgenic leaves (FIG. 6c) increased rapidly, reaching approximately twice the size of control non transgenic WT leaves (FIG. 6a) or control transgenic sense leaves (FIG. 6b). As shown in FIGS. 6d-e, a significant difference was also observed in the necrotic lesions developed on stems of transgenic LeChrC-suppressed plants (FIG. 6e) vs. control, non-transgenic ones (FIG. 6d). Whereas the lesions on the control plants remained restricted in size, those on LeChrC-suppressed plants spread, covering up to 60% more area (vs. controls), 8 days post-inoculation. Mock-inoculated plants did not generate lesions on either stems or leaves. Moreover, as shown in Table 2 below, and in FIG. 6b, plants of a tomato transgenic line characterized by Vishnevetsky et al. (Plant J. 20, 423-431, 1999) that overaccumulates ChrC (sense in Table 2 below) were significantly less susceptible to B. cinerea infection, as compared to both control non-transgenic plants and LeChrC-suppressed plants (independent lines 11, 13 and 37 in Table 2), further indicating the involvement of LeChrC in the plant's resistance to the fungus. FIG. 6f shows that following inoculation with B. cinerea, no expression of LeChrC was detected in RNAi-transgenic plants, whereas in control WT plants, and transgenic sense lines, LeChrC transcript levels increased.

TABLE 2

| line | Disease severity on leaves: 3 days (%) | Disease severity on leaves: 6 days (%) |
|---|---|---|
| Sense | 0.6 c | 3.6 c |
| 11 | 1.6 b | 19.0 a |
| 13 | 1.2 b | 15.0 a |
| 37 | 1.9 a | 19.0 a |
| WT | 0.9 c | 6.5 b |

Numbers followed by a common letter are not significantly different (t test, $P \leq 0.05$).

TABLE 3

| Line | Disease severity on leaves (%) | | Lesion size on stem (mm) | |
|---|---|---|---|---|
| | 3 days | 6 days | 6 days | 8 days |
| Sense | 3.5 b | 21.5 c | 12.6 d | 21.7 d |
| 11 | 6.4 b | 89.8 a | 35.5 a | 43.7 ab |
| 13 | 3.4 b | 83.5 a | 29.3 b | 47.3 a |
| 37 | 5.0 b | 86.8 a | 22.2 c | 37.0 b |
| WT | 4.6 b | 54.8 b | 28.7 b | 28.7 c |

Numbers followed by a common letter are not significantly different (t test, $P \leq 0.05$).

Taken together, results show that transgenic plants with suppressed LeChrC were significantly more susceptible to infection in both in-vitro experiments with detached leaves and in whole plants with intact leaves and stems. Conversely, ChrC overexpressing plants were less susceptible to infection. These results further confirm that LeChrC expression is needed for resistance to B. cinerea infection. Without being bound to theory, since oxidative events are strongly implicated in the interaction of B. cinerea with plants (Malolepsza, Plant Pathol. 54, 317-324, 2005), LeChrC might act in this process in sequestering hydrophobic compounds as part of the plants reaction against oxidative stress inflicted by the pathogens.

Example 3

Activation of the ChrC Promoter

Materials and Experimental Procedures

Isolation of MYBYS, a regulatory factor interacting with the ChrC promoter—In floral tissues, expression of ChrC depends on a factor that is transcriptionally up-regulated by the hormone gibberellin (GA; Vishnevetsky et al., Plant J. 20, 423-431, 1999). With the aim of identifying regulatory factors interacting with the ChrC promotor, a λZap-cDNA expression library from stage 3 cucumber flower corollas (as described in Vishnevetsky et al., Plant J. 10, 1111-1118, 1996) was screened with a radiolabeled region of the ChrC promoter (SEQ ID NO: 5; 137-bp, positions −215 to −78 of SEQ ID NO: 33).

Generation of partial ChrC constructs—In order to characterize activation of the ChrC promoter, constructs containing partial sequences of the ChrC promoter were generated. The ChrC:GUS construct, containing 3,500 bp of the ChrC promoter (SEQ ID NO: 31) upstream of the GUS gene, was generated as previously described (pGEM3Z/201.2; Vishnevetsky et al., Plant J. 20, 423-431, 1999). Δ212ChrC:GUS was generated by digesting ChrC:GUS (EheI and EcoRI), thus generating a 212 bp deletion between positions −290 and −78 of the promoter (the deleted fragment being SEQ ID NO: 6). 212ChrC:GUS was generated by introducing the above mentioned 212-bp fragment released from the ChrC promoter region, 5' to a minimal (−46 to +8, SEQ ID NO: 34) TATA-box promoter fused to a GUS (TATA:GUS). See table 4 below.

To detail $GA_3$-responsive cis-elements in the ChrC promoter, a series of vectors, as shown in FIG. 7a, and Table 4 below, aimed at characterizing the above described 212-bp sequence, were effected by modifying the promoter area in 212ChrC:GUS. A plasmid containing a 137 bp promoter fragment (137ChrC:GUS containing SEQ ID NO: 5) was generated by digestion of 212ChrC:GUS (PmaCI and ApoI) and blunt ligation of the generated promoter fragment (−215 to −78) to TATA:GUS. Plasmids containing promoter fragments −141 to −78 (63 bp, SEQ ID NO: 7) and −124 to −78 (46 bp, SEQ ID NO: 8) fused to TATA:GUS, were effected by fusing PCR fragments of the relevant promoter regions, amplified with the following primers: F-63 (5'-GACCTC-CAAAACAACGACA-3' SEQ ID NO: 16) and R (5'-TCACGGGTTGGGGTTTCTAC-3', SEQ ID NO: 17) for the 63 bp fragment; and F-46 (5'-CAAGTTTCCGAA-CAGTCGCG-3' SEQ ID NO: 18) and R (SEQ ID NO: 17), for the 46 bp fragment.

Mutagenesis was effected, as described in FIGS. 8a-b, within the −141 to −124 promoter fragment. A 6-bp sequence, GTA TCT (SEQ ID NO: 19), was used to replace the original sequence of the promoter on four adjacent regions (six nucleotides each) with three-base gaps between each of the four (MG1-MG4) mutations. Mutation was generated using primers containing the GTATCT replacement of the promoter sequence: MG1 (5'-GACGTATCTAACAACGA-CAAGTTTCCGAA-3', SEQ ID NO: 21), MG2 (5'-GAC-CTCGTATCTAACGACAAGTTTCCGAA-3', SEQ ID NO: 22), MG3 (5'-GACCTCCAAGTATCTGACAAGTTTC-CGAA-3', SEQ ID NO: 23), and MG4 (5'-GACCTC-CAAAACGTATCTAAGTTTCCGAA-3', SEQ ID NO: 24, see also Table 4 below).

Generation of a construct containing MYBYS—The 35S:MYBYS construct containing the MYBYS transcription factor gene, under the regulation of cauliflower mosaic virus (CaMV) 35S, was generated by introducing the mybys gene sequence (SEQ ID NO: 3) into a PCD vector (Broido et al., Exp. Cell Res. 192, 248-255, 1991) 3' to the CaMV 35S promoter.

Identification of $GA_3$-responsive cis-elements in the ChrC promoter—In order to identify the $GA_3$-responsive cis-elements in the ChrC promoter, young cucumber flower buds were subjected to particle bombardment of the above described constructs containing partial ChrC promoters, following treatment with GA$_3$ or water. GA$_3$ or water treatments were effected with the Biolistic PDS 1000/He system (Bio-Rad, Hercules, Calif.) at a pressure of 1,350 dpi (effector to reporter taken in 1:1 molar ratio), as described by Vishnevetsky et al. (Plant J. 20, 423-431, 1999). Twenty four hours following treatment, leaves and petals were evaluated. A construct containing CaMV 35S promoter fused to green fluorescent protein (pEGFP-PL vector; as described in Ben-Nissan et al., Plant J. 37, 229-238, 2004) was co-bombarded and used to normalize the transient GUS expression results. Following bombardment, tissue was incubated for a few hours at 37° C. in a 0.1% (w/v) X-Gluc (5-bromo-4-chloro-3-indolyl b-D-GlcUA; Duchefa, Haarlem, The Netherlands) solution containing 0.1 M sodium phosphate buffer, pH 7.0, 10 mM EDTA, and 0.1% (w/v) Triton X-100. Prior to transfer of the tissue to the X-Gluc solution, GFP expression was monitored using a fluorescence binocular (480/40 nm excitation filter and 510 nM barrier filter; MZ FLIII; Leica) equipped with a DC300FX camera (Leica), GUS expression was normalized to GFP using ImageJ software (Bezanilla et al., Plant Physiol. 133, 470-474, 2003). All experiments were repeated at least five times.

MYBYS transient activation assays—To assess whether MYBYS can activate ChrC promoter, young green transgenic tomato flowers constitutively expressing 35S:MYBYS (independent transgenic lines 4, 10, and 110) were bombardment with ChrC:GUS, and analyzed for ChrC expression. Expression of ChrC was analyzed histochemicaly (on transgenic line 10), as well as with RNA blot, as described in Example 1 above, using, in addition to the ChrC probe, a probe generated from a fragment of the 3' end of the mybys gene (nucleotides 456-970 of SEQ ID NO: 28). A transgenic line with no expression of MYBYS (line 3), and nontransgenic flowers (WT) bombarded with ChrC:GUS were used as controls.

To assess whether MYBYS can activate ChrC promoter in floral tissue irrespective of chromoplastogenesis, chromoplast-lacking petunia (Petunia hybrida) corollas were cobombarded with 35S:MYBYS, and 137ChrC:GUS (containing the 137pb promoter fragment) or ChrC:GUS (containing the 3,500 bp promoter fragment). As controls, corollas were bombarded with 137ChrC:GUS or ChrC:GUS alone. Additional controls included cobombardment of 35S:MYBYS with the minimal TATA-box promoter fused to GUS (TATA:GUS), or with the unrelated promoter construct glutathione S-transferase:GUS (as described in Zenvirt, M. Sc. thesis. The Hebrew University of Jerusalem, Jerusalem, Israel 2000), and cobombardment of ChrC:GUS or 137ChrC:GUS with the transcriptional regulator Pap1 (production of anthocyanin pigment 1, which regulates the anthocyanin pathway) fused to CaMV 35S (35S:PAP vector; as described in Ben-Meir, Ph.D. thesis. The Hebrew University of Jerusalem, Jerusalem, Israel 2003), as a control MYB factor. Following bombardment, tissue was incubated with the X-Gluc solution as described above. Similar transient-expression assays were also effected in carnation (Dianthus caryophyllus) and gypsophila (Gypsophila paniculata), which do not accumulate chromoplasts.

In vitro flower bud culture—In vitro culture of cucumber flower buds was performed as described previously (Vishnevetsky et al., J. Biol. Chem. 272, 24747-24750, 1997). Stage 1 flower buds were cultured in double distilled water for 12 h and then transferred to fresh double distilled water or 100 mM GA$_3$ (Sigma-Aldrich) for another 12 h prior to bombardment.

Results

GA-Responsive Element within the ChrC Promoter—Expression assays of constructs including partial promoter sequences, during exposure to GA$_3$, were effected in order to identify specific sequences in the ChrC promoter which react to GA$_3$. As shown in FIG. 7a, and as summarized in Table 4 below, whereas the 212, 137, and 63-bp fragments of ChrC promoter were responsive to GA$_3$, showing 3- to 4-fold higher GUS activity in GA$_3$ versus water treatment, the 46-bp fragment was not affected by GA$_3$. Interestingly, this 46-bp fragment drove high GUS expression in control, water-treated corollas, suggesting that there may be a GA$_3$-responsive repressor acting via a cis-element within the 18-bp region at the 5' end of the 63-bp promoter region (between −141 and −124; SEQ ID NO: 32). FIG. 7b additionally shows that GUS expression was similarly high in both water- and GA$_3$-treated corollas when the vector with the deletion of the entire 212-bp region of ChrC promoter was used, further supporting repressor-mediated regulation of ChrC promoter by GA$_3$. In order to further investigate and identify the necessary elements for the promotor's response to GA$_3$ activation expression assays were effected with mutated promoter sequences. FIG. 8b and Table 4 below, show that one construct (MG1) containing a mutation between −138 and −133, upon delivery to young flower corollas, yielded similarly high GUS expression in both water- and GA$_3$-treated corollas, whereas other constructs, including the one with a mutation between −135 to −130 (MG2), were still responsive to GA$_3$ in a manner similar to that of the control nonmutated promoter. These results point to the three bases, CTC (SEQ ID NO: 27), between −138 and −136 as necessary elements for the response of ChrC promoter to GA$_3$ activation. It should be noted that none of these analyzed mutations in the 18-bp region affected activation of the ChrC promoter by MYBYS, suggesting that this trans-factor acts through different cis-elements present in the promoter

TABLE 4

| Name of plasmid | SEQ ID NO: of promoter plasmid comprising the fragment set forth in: | Length | Positions in the promoter sequence (SEQ ID NO: 33) | Promoter activity |
|---|---|---|---|---|
| 212ChrC:GUS | SEQ ID NO: 6 | 212 | −290 to −78 | inducible |
| 137ChrC:GUS | SEQ ID NO: 5 | 137 | −215 to −78 | inducible |
| 63ChrC:GUS | SEQ ID NO: 7 | 63 | −141 to −78 | inducible |
| 46ChrC:GUS | SEQ ID NO: 8 | 46 | −124 to −78 | constitutive |
| MG1 | SEQ ID NO: 35 | 63 mutation −138-133 | −141 to −−78 | constitutive |
| MG2 | SEQ ID NO: 36 | 63 mutation −135-130 | −141 to −78 | inducible |
| MG3 | SEQ ID NO: 37 | 63 mutation −132-127 | −141 to −78 | inducible |
| MG4 | SEQ ID NO: 9 | 63 mutation −129-124 | −141 to −78 | inducible |

MYB-Like Factor MYBYS Activates the ChrC Promoter—Screening of a cucumber expression library with a radiolabeled region of the ChrC promoter (SEQ ID NO: 5) revealed that the promoter interacts with a MYB-like transcription factor, shown in FIG. 9a, having a typical DNA-binding domain containing the helix-turn-helix conserved R2 and R3 repeats (underlined in FIG. 9a). This transcription factor was termed MYBYS (MYBlike, SEQ ID NO: 29; GenBank Accession No. DQ311672). As shown in FIG. 9a, C-terminal to the DNA binding domain, MYBYS contains a motif of amino acids (Gln and Pro) that is frequently associated with activation domains (amino acids 197-202 of SEQ ID NO: 29). FIG. 9b shows that mybys expression at the RNA level in floral tissue accumulates in parallel to flower development, up to anthesis, at which stage no transcript was revealed. No expression was detected in leaf tissues. This spatial and temporal pattern of expression is essentially identical to that of ChrC.

MYBYS transcription factor specifically activates the ChrC promoter—The activation of the ChrC promoter was analyzed by trans-activation assays of constructs expressing the promoter and the transcription factor. FIG. 10a shows trans activation of the ChrC promoter by MYBYS, irrespective of chromoplastogenesis, as GUS is expressed in chromoplast-lacking petunia corollas following cobombardment with 35S:MYBYS and 137ChrC:GUS or ChrC:GUS. No GUS expression was observed in petunia corollas following bombardment with 137ChrC:GUS or ChrC:GUS alone, or when they were cobombarded with unrelated MYBs driven by CaMV 35S (35S:PAP or 35S:Lc). GUS expression was additionally not observed when 35S:MYBYS was cobombarded with a minimal TATA-box promoter fused to GUS or with the unrelated promoter construct glutathione S-transferase:GUS. In leaves, MYBYS was not sufficient for ChrC:GUS trans-activation. The same results, i.e. trans-activation of 137ChrC:GUS or ChrC:GUS specifically by MYBYS, were obtained when similar transient-expression assays were done on other flowers that accumulate anthocyanin and not carotenoids, carnation (*Dianthus caryophyllus*) and gypsophila (*Gypsophila paniculata*). Thus, MYBYS was shown to specifically trans-activate the ChrC promoter, independent of chromoplastogenesis.

Expression of ChrC and MYBYS in transgenic plants constitutively expressing MYBYS—The control of the ChrC promoter by MYBYS was further demonstrated in transgenic tomato flower corollas constitutively expressing MYBYS. FIG. 10b shows that bombardment of young green tomato flower corollas with ChrC promoter expressing constructs 137ChrC:GUS or ChrC:GUS, yielded GUS expression in MYBYS-transgenic flowers but not in control plants. FIG. 10c shows that expression of mybys in young corollas of T2-generation transgenic plants, as compared to control non-transgenic ones, was further confirmed by RNA blot analysis. It should be noted that at this early stage of flower development, endogenous PAP is not yet expressed (Vishnevetsky, Plant J. 20, 423-431, 1999), therefore any expression of ChrC is due to the exogenous gene alone.

Given together, the results confirm that MYBYS acts to regulate the ChrC promoter. Its expression is spatially controlled with no detectable levels in leaves. In floral tissue, it is temporally regulated, mimicking the increase in ChrC levels during flower development.

Regulation at the RNA level has been shown to control PAPs in diverse processes/tissues, i.e. developmental and hormonal expression and induction by biotic and abiotic stresses of both ChrC and Fib (FIGS. 3a-b; Kuntz et al., Plant J. 13, 351-361, 1998; Vishnevetsky et al., Plant J. 20, 423-431, 1999). Without being bound to theory, and as previously proposed (Vishnevetsky et al., Plant J. 20, 423-431, 1999), while the type or amount of carotenoids exerts a posttranscriptional effect on ChrC expression, MYBYS may act as an isoprenoid pathway-related flower-specific trans-factor, which modulates the ChrC promoter at the transcriptional level.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications and GenBank Accession numbers mentioned in this specification are herein incorporated in their entirety by reference into the specification, to the same extent as if each individual publication, patent or patent application or GenBank Accession number was specifically and individually indicated to be incorporated herein by reference. In addition, citation or identification of any reference in this application shall not be construed as an admission that such reference is available as prior art to the present invention.

What is claimed is:

1. A method of increasing the tolerance of a plant to a biotic or an abiotic stress, the method comprising transforming the plant with a DNA construct comprising a nucleic acid encoding the exogenous MYBYS as set forth in SEQ ID NO: 29, thereby increasing the tolerance of the plant to the biotic or the abiotic stress.

2. The method of claim 1 further comprising transforming the plant with a second DNA construct comprising a nucleic acid encoding an exogenous fibrillin/CDSP34.

3. The method of claim 2 further comprising subjecting the plant to gibberellin, so as to increase said fibrillin/CDSP34 expression in the plant.

4. The method of claim 2, wherein said fibrillin/CDSP34 is set forth in SEQ ID NO: 3 or 26.

5. The method of claim 1, wherein said DNA construct further comprises at least one promoter capable of directing transcription of said nucleic acid in said plant.

* * * * *

SEQUENCE LISTING

```
<160> NUMBER OF SEQ ID NOS: 37

<210> SEQ ID NO 1
<211> LENGTH: 776
<212> TYPE: DNA
<213> ORGANISM: Lycopersicon esculentum

<400> SEQUENCE: 1
tgctctttct ctgtttcact ctgaaaatgg cttccatctc ttctctcaat caaattcctt     60
gcagaactct ccaaattaca tcccaatatt caaaacccac ctccaaaatc tcaactttac    120
ccatctcctc cacgaatttc ccatcaaaaa cagaactaca cagagcaatt tcagtcaaag    180
```

-continued

```
aattcacata cccaaaacca aaattcacag ctcaagccac aaattacgac aaggaagatg      240
agtgggggcc ggaagtggag aaaataagtc cgggtggagt agcggttgtg gatgaagaac      300
caccaaagga gccaagtgaa attgagttgc tgaagaagca attggcggat tcttttatg      360 gaaccaatag gggtttgagt gctagcagtg agactagggc ggaaatcgtt gaactcatca      420
cacagcttga gtcgaagaac cctaatccag cacctactga agccttgact cttctcaacg      480
gcaaatggat tcttgcgtac acatcttttt cgggtttgtt ccccttgttg tcacggggca      540
atctgcttct ggttcgagtt gaagagattt cacagactat cgattctgag agtttcactg      600
tccaaaactc tgttgtcttt gctggacctt agctacaac ttccattagt accaatgcca      660
aattcgaagt cagaagtcca aaacgcgtcc agattaaatt cgaagaaggc ataattggaa      720
caccccagtt gacagattcc atcgtattgc ctgagaacgt tgaattcttg ggacaa         776
```

<210> SEQ ID NO 2
<211> LENGTH: 1114
<212> TYPE: DNA
<213> ORGANISM: Lycopersicon esculentum

<400> SEQUENCE: 2

```
tagcattctg ctctttctct gtttcactct gaaaatggct tccatctctt ctctcaatca      60
aattccttgc agaactctcc aaattacatc ccaatattca aacccacct ccaaaatctc       120 aactttaccc atctcctcca cgaatttccc atcaaaaaca gaactacaca gagcaatttc      180
agtcaaagaa ttcacatacc caaaaccaaa attcacagct caagccacaa attacgacaa      240
ggaagatgag tggggccgg aagtggagaa ataagtccg ggtggagtag cggttgtgga       300
tgaagaacca ccaaaggagc caagtgaaat tgagttgctg aagaagcaat tggcggattc      360
tttttatgga accaataggg gtttgagtgc tagcagtgag actagggcgg aaatcgttga      420
actcatcaca cagcttgagt cgaagaaccc taatccagca cctactgaag ccttgactct      480
tctcaacggc aaatggattc ttgcgtacac atcttttcg ggtttgttcc ccttgttgtc      540
acggggcaat ctgcttctgg ttcgagttga agagatttca cagactatcg attctgagag      600
tttcactgtc caaaactctg ttgtctttgc tggacctta gctacaactt ccattagtac      660
caatgccaaa ttcgaagtca gaagtccaaa acgcgtccag attaaattcg aagaaggcat      720
aattggaaca ccccagttga cagattccat cgtattgcct gagaacgttg aattcttggg      780
acaaaagatt gatctaagcc ccttcaaagg cttgattact tcagtccaag acacagcttc      840
ctcggtggcc aagtccattt caagtcaacc accaattaag tttcctattt ccaataacaa      900
tgcacaatca tggctgctga acctactt ggatgatgag cttaggatct ccagaggaga       960
tgctggcagt gtatttgtgt tgatcaagga aggcagtccc ctcttgaagc cttaaaagac      1020
acatgttttt ggagttatgt ttttcatcat aatataggag agcaaacact agaaagtaaa      1080
aaaatatgat gtaaactaaa aataagtttt cctc                                 1114
```

<210> SEQ ID NO 3
<211> LENGTH: 326
<212> TYPE: PRT
<213> ORGANISM: Lycopersicon esculentum

<400> SEQUENCE: 3

```
Met Ala Ser Ile Ser Ser Leu Asn Gln Ile Pro Cys Arg Thr Leu Gln
1               5                   10                  15

Ile Thr Ser Gln Tyr Ser Lys Pro Thr Ser Lys Ile Ser Thr Leu Pro
            20                  25                  30
```

```
Ile Ser Ser Thr Asn Phe Pro Ser Lys Thr Glu Leu His Arg Ala Ile
        35                  40                  45

Ser Val Lys Glu Phe Thr Tyr Pro Lys Pro Lys Phe Thr Ala Gln Ala
 50                  55                  60

Thr Asn Tyr Asp Lys Glu Asp Glu Trp Gly Pro Glu Val Glu Lys Ile
 65                  70                  75                  80

Ser Pro Gly Gly Val Ala Val Asp Glu Glu Pro Pro Lys Glu Pro
                 85                  90                  95

Ser Glu Ile Glu Leu Leu Lys Lys Gln Leu Ala Asp Ser Phe Tyr Gly
             100                 105                 110

Thr Asn Arg Gly Leu Ser Ala Ser Glu Thr Arg Ala Glu Ile Val
             115                 120                 125

Glu Leu Ile Thr Gln Leu Glu Ser Lys Asn Pro Asn Pro Ala Pro Thr
130                 135                 140

Glu Ala Leu Thr Leu Leu Asn Gly Lys Trp Ile Leu Ala Tyr Thr Ser
145                 150                 155                 160

Phe Ser Gly Leu Phe Pro Leu Leu Ser Arg Gly Asn Leu Leu Val
                 165                 170                 175

Arg Val Glu Glu Ile Ser Gln Thr Ile Asp Ser Glu Ser Phe Thr Val
             180                 185                 190

Gln Asn Ser Val Val Phe Ala Gly Pro Leu Ala Thr Thr Ser Ile Ser
             195                 200                 205

Thr Asn Ala Lys Phe Glu Val Arg Ser Pro Lys Arg Val Gln Ile Lys
210                 215                 220

Phe Glu Glu Gly Ile Ile Gly Thr Pro Gln Leu Thr Asp Ser Ile Val
225                 230                 235                 240

Leu Pro Glu Asn Val Glu Phe Leu Gly Gln Lys Ile Asp Leu Ser Pro
                 245                 250                 255

Phe Lys Gly Leu Ile Thr Ser Val Gln Asp Thr Ala Ser Ser Val Ala
             260                 265                 270

Lys Ser Ile Ser Ser Gln Pro Pro Ile Lys Phe Pro Ile Ser Asn Asn
             275                 280                 285

Asn Ala Gln Ser Trp Leu Leu Thr Thr Tyr Leu Asp Asp Glu Leu Arg
290                 295                 300

Ile Ser Arg Gly Asp Ala Gly Ser Val Phe Val Leu Ile Lys Glu Gly
305                 310                 315                 320

Ser Pro Leu Leu Lys Pro
                 325

<210> SEQ ID NO 4
<211> LENGTH: 531
<212> TYPE: DNA
<213> ORGANISM: Lycopersicon esculentum

<400> SEQUENCE: 4
atggcttcca tctcttctct caatcaaatt ccttgcagaa ctctccaaat tacatcccaa      60
tattcaaaac ccacctccaa aatctcaact ttacccatct cctccacgaa tttcccatca     120
aaaacagaac tacacagagc aatttcagtc aaagaattca catacccaaa accaaaattc     180
acagctcaag ccacaaatta cgacaaggaa gatgagtggg gaccggaagt ggagaaaata     240
agtccgggtg gagtagcggt tgtggatgaa gaaccaccaa aggagccaag tgaaattgag     300
ttgctgaaga gcaattggc ggattctttt tatggaacca ataggggttt gagtgctagc     360
agtgagacta gggcgaaaat cgttgaactc atcacacagc ttgagtcgaa gaaccctaat     420
ccagcaccta ctgaagcctt gactcttctc aacggcaaat ggattcttgc gtacacatct     480
```

-continued ttttcgggtt tgttcccctt gttgtcacgg ggcaatctgc ttctggttcg a    531

<210> SEQ ID NO 5
<211> LENGTH: 137
<212> TYPE: DNA
<213> ORGANISM: Cucumis sativus
<220> FEATURE:
<221> NAME/KEY: misc_feature
<222> LOCATION: (1)..(137)
<223> OTHER INFORMATION: C. sativus ChrC partial promoter sequence

<400> SEQUENCE: 5
gtgttctgag cttaacaagc cacgttgcgt gccattgcca aacgagtcat tttaacttca    60
caaggtccga tttgacctcc aaaacaacga caagtttccg aacagtcgcg aagatcaagg    120
gtataatcgt cttttg    137

<210> SEQ ID NO 6
<211> LENGTH: 212
<212> TYPE: DNA
<213> ORGANISM: Cucumis sativus
<220> FEATURE:
<221> NAME/KEY: misc_feature
<222> LOCATION: (1)..(212)
<223> OTHER INFORMATION: C. sativus ChrC partial promoter sequence

<400> SEQUENCE: 6
gcctcacatg cttcggttgg ctcgctttag tctctgcctt ctttgtattt tgtactcccc    60
ctcttcctgt gccacgtgtt ctgagcttaa caagccacgt tgcgtgccat tgccaaacga    120 gtcatttaa cttcacaagg tccgatttga cctccaaaac aacgacaagt ttccgaacag    180
tcgcgaagat caagggtata atcgtctttt tg    212

<210> SEQ ID NO 7
<211> LENGTH: 63
<212> TYPE: DNA
<213> ORGANISM: Cucumis sativus
<220> FEATURE:
<221> NAME/KEY: misc_feature
<222> LOCATION: (1)..(63)
<223> OTHER INFORMATION: C. sativus ChrC partial promoter sequence

<400> SEQUENCE: 7
gacctccaaa acaacgacaa gtttccgaac agtcgcgaag atcaagggta taatcgtctt    60
ttt    63

<210> SEQ ID NO 8
<211> LENGTH: 46
<212> TYPE: DNA
<213> ORGANISM: Cucumis sativus
<220> FEATURE:
<221> NAME/KEY: misc_feature
<222> LOCATION: (1)..(46)
<223> OTHER INFORMATION: C. sativus ChrC partial promoter sequence

<400> SEQUENCE: 8
caagtttccg aacagtcgcg aagatcaagg gtataatcgt cttttt    46

<210> SEQ ID NO 9
<211> LENGTH: 63
<212> TYPE: DNA
<213> ORGANISM: Artificial sequence
<220> FEATURE:
<223> OTHER INFORMATION: MG4 mutant of the cucumber ChrC promoter

<400> SEQUENCE: 9

```
gacctccaaa acgtatctaa gtttccgaac agtcgcgaag atcaagggta taatcgtctt    60
ttt                                                                  63

<210> SEQ ID NO 10
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 10
tgctctttct ctgtttcact ctga                                           24

<210> SEQ ID NO 11
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 11
ttgtcccaag aattcaacgt tc                                             22

<210> SEQ ID NO 12
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 12
atggcttcca tctcttctct ca                                             22

<210> SEQ ID NO 13
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 13
tcgaaccaga agcagattgc                                                20

<210> SEQ ID NO 14
<211> LENGTH: 17
<212> TYPE: DNA
<213> ORGANISM: Artificial sequence
<220> FEATURE:
<223> OTHER INFORMATION: Single strand DNA oligonucleotide

<400> SEQUENCE: 14
ggttttgctg gggatgc                                                   17

<210> SEQ ID NO 15
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 15
cattgaatgt ctcaaacagt atttgagtc                                      29

<210> SEQ ID NO 16
<211> LENGTH: 19
```

```
<212> TYPE: DNA
<213> ORGANISM: Artificial sequence
<220> FEATURE:
<223> OTHER INFORMATION: Single strand DNA oligonucleotide

<400> SEQUENCE: 16
gacctccaaa acaacgaca                                                   19

<210> SEQ ID NO 17
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 17
tcacgggttg gggtttctac                                                  20

<210> SEQ ID NO 18
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 18
caagtttccg aacagtcgcg                                                  20

<210> SEQ ID NO 19
<211> LENGTH: 6
<212> TYPE: DNA
<213> ORGANISM: Artificial sequence
<220> FEATURE:
<223> OTHER INFORMATION: Sequence used as a substitute in the
      mutagenesis of the c. Sativa promoter constructs

<400> SEQUENCE: 19 gtatct                                                                  6

<210> SEQ ID NO 20
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 20
ctatccttcg caagacccttt cc                                              22

<210> SEQ ID NO 21
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 21
gacgtatcta acaacgacaa gtttccgaa                                        29

<210> SEQ ID NO 22
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 22
```

-continued

```
gacctcgtat ctaacgacaa gtttccgaa                                                29
```

<210> SEQ ID NO 23
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 23

```
gacctccaag tatctgacaa gtttccgaa                                                29
```

<210> SEQ ID NO 24
<211> LENGTH: 29
<212> TYPE: DNA
<213> ORGANISM: Artificial sequence
<220> FEATURE:
<223> OTHER INFORMATION: Single strand DNA oligonucleotide

<400> SEQUENCE: 24

```
gacctccaaa acgtatctaa gtttccgaa                                                29
```

<210> SEQ ID NO 25
<211> LENGTH: 322
<212> TYPE: PRT
<213> ORGANISM: Capsicum annuum

<400> SEQUENCE: 25

Met Ala Ser Ile Ser Ser Leu Asn Gln Ile Pro Cys Lys Thr Leu Gln
1               5                   10                  15

Ile Thr Ser Gln Tyr Ser Lys Ile Ser Ser Leu Pro Leu Thr Ser Pro
            20                  25                  30

Asn Phe Pro Ser Lys Thr Glu Leu His Arg Ser Ile Ser Ile Lys Glu
        35                  40                  45

Phe Thr Asn Pro Lys Pro Lys Phe Thr Ala Gln Ala Thr Asn Tyr Asp
    50                  55                  60

Lys Glu Asp Glu Trp Gly Pro Glu Leu Glu Gln Ile Asn Pro Gly Gly
65                  70                  75                  80

Val Ala Val Val Glu Glu Pro Pro Lys Glu Pro Ser Glu Met Glu
                85                  90                  95

Lys Leu Lys Lys Gln Leu Thr Asp Ser Phe Tyr Gly Thr Asn Arg Gly
            100                 105                 110

Leu Ser Ala Ser Ser Glu Thr Arg Ala Glu Ile Val Glu Leu Ile Thr
        115                 120                 125

Gln Leu Glu Ser Lys Asn Pro Thr Pro Ala Pro Thr Glu Ala Leu Ser
    130                 135                 140

Leu Leu Asn Gly Lys Trp Ile Leu Ala Tyr Thr Ser Phe Ser Gly Leu
145                 150                 155                 160

Phe Pro Leu Leu Ala Arg Gly Asn Leu Leu Pro Val Arg Val Glu Glu
                165                 170                 175

Ile Ser Gln Thr Ile Asp Ala Glu Thr Leu Thr Val Gln Asn Ser Val
            180                 185                 190

Val Phe Ala Gly Pro Leu Ser Thr Thr Ser Ile Ser Thr Asn Ala Lys
        195                 200                 205

Phe Glu Val Arg Ser Pro Lys Arg Leu Gln Ile Asn Phe Glu Glu Gly
    210                 215                 220

Ile Ile Gly Thr Pro Gln Leu Thr Asp Ser Ile Glu Leu Pro Glu Asn
225                 230                 235                 240

Val Glu Phe Leu Gly Gln Lys Ile Asp Leu Ser Pro Phe Lys Gly Leu

```
            245                 250                 255
Ile Thr Ser Val Gln Asp Thr Ala Thr Ser Val Ala Lys Ser Ile Ser
                260                 265                 270

Ser Gln Pro Pro Ile Lys Phe Pro Ile Ser Asn Ser Tyr Ala Gln Ser
            275                 280                 285

Trp Leu Leu Thr Thr Tyr Leu Asp Ala Glu Leu Arg Ile Ser Arg Gly
        290                 295                 300

Asp Ala Gly Ser Ile Phe Val Leu Ile Lys Glu Gly Ser Pro Leu Leu
305                 310                 315                 320

Lys Pro

<210> SEQ ID NO 26
<211> LENGTH: 322
<212> TYPE: PRT
<213> ORGANISM: Cucumis sativus

<400> SEQUENCE: 26

Met Ala Phe Val Ser Gln Phe Asn Gln Leu Pro Cys Lys Thr Leu Ala
1               5                   10                  15

Leu Asn Pro Pro Gln Pro Gln Leu Thr Ser Lys Pro Ser Val Phe Pro
            20                  25                  30

Ile Ala Ser Ile Gly Ala Thr Ala Arg Ala Ala Gly Lys Ser Leu
        35                  40                  45

Ile Ser Val Arg Pro Ala Phe Lys Val Arg Ala Val Leu Asn Asp Asp
    50                  55                  60

Glu Trp Gly Glu Asp Lys Asp Glu Lys Tyr Gly Asp Asp Ser Ser Val
65                  70                  75                  80

Ala Val Ala Glu Lys Glu Glu Lys Pro Leu Glu Pro Ser Glu Ile
                85                  90                  95

Tyr Lys Leu Lys Lys Ala Leu Val Asp Ser Phe Tyr Gly Thr Asp Arg
                100                 105                 110

Gly Leu Arg Val Ser Arg Asp Thr Arg Ala Glu Ile Val Glu Leu Ile
            115                 120                 125

Thr Gln Leu Glu Ser Lys Asn Pro Thr Pro Ala Pro Thr Glu Ala Leu
        130                 135                 140

Thr Leu Leu Asn Gly Lys Trp Ile Leu Ala Tyr Thr Thr Phe Ala Gly
145                 150                 155                 160

Leu Phe Pro Leu Leu Ser Arg Asn Leu Pro Leu Val Lys Val Glu Glu
                165                 170                 175

Ile Ser Gln Thr Ile Asp Ser Glu Asn Leu Thr Val Gln Asn Ser Val
            180                 185                 190

Gln Phe Ser Gly Pro Leu Ala Thr Thr Ser Ile Thr Thr Asn Ala Lys
        195                 200                 205

Phe Glu Val Arg Ser Pro Leu Arg Val His Ile Lys Phe Glu Glu Gly
    210                 215                 220

Val Ile Gly Thr Pro Gln Leu Thr Asp Ser Ile Val Ile Pro Asp Asn
225                 230                 235                 240

Val Asp Phe Leu Gly Gln Lys Ile Asp Phe Thr Pro Phe Asn Gly Ile
                245                 250                 255

Ile Ser Ser Leu Gln Asp Thr Ala Ser Asn Val Ala Lys Thr Ile Ser
            260                 265                 270

Ser Gln Pro Pro Ile Lys Phe Ser Ile Ser Asn Thr Arg Val Glu Ser
        275                 280                 285

Trp Leu Leu Thr Thr Tyr Leu Asp Glu Asp Leu Arg Ile Ser Arg Gly
    290                 295                 300
```

```
Asp Gly Gly Ser Val Phe Val Leu Leu Lys Glu Gly Ser Ser Phe Leu
305                 310                 315                 320

Ser Leu

<210> SEQ ID NO 27
<211> LENGTH: 3
<212> TYPE: DNA
<213> ORGANISM: Cucumis sativus
<220> FEATURE:
<221> NAME/KEY: misc_feature
<222> LOCATION: (1)..(3)
<223> OTHER INFORMATION: Nucleotides corresponding to -138 to -136 that
      constitute a necessary element for the response of ChrC promoter
      to GA3 activation

<400> SEQUENCE: 27 ctc                                                                      3

<210> SEQ ID NO 28
<211> LENGTH: 993
<212> TYPE: DNA
<213> ORGANISM: Cucumis sativus
<220> FEATURE:
<221> NAME/KEY: misc_feature
<222> LOCATION: (972)..(972)
<223> OTHER INFORMATION: n is a, c, g, or t

<400> SEQUENCE: 28
atcgttgttg ttgttccact gaagtgaaga attagggaaa atatatataa agcaaatata        60
agtttaaaag aagagaagag gaaaatggga aggcctccat gttgtgagaa agtagggata       120
aagaaagggc catggactcc tgaagaagat atcattcttg tttcttacat tcaacaacat       180
ggtcctggca attggagatc agttcctact aacacaggat tgttgcgttg tagcaaaagt       240
tgtagactta gatggaccaa ttatcttaga cctggaatta aaagaggcaa tttcactcct       300
catgaagaag gaatgatcat tcatcttcaa gctttattgg gtaacaaatg ggcggcgata       360
gcttcgtacc ttcctcaaag aacagataat gatatcaaga attattggaa cactcacttg       420
aaaaagaagc ttaaaaagtt gaattccgcc gccgtcgaca ccccggagcc gcctgaatcc       480
gccaccactc gctttcaatc caatgataaa gttccgactg ctgattcacc ctcgtcgcta       540
gtttcaaaca gagccaccac ttacgcctca agtgccgaga catttcccg gcttcttcaa        600 gcttggatga gatcttcacc ggaggaatct cgacggaaaa tgagcggtga gaattctata       660
gccgccgcca cgcagcagca gcagcagccg aaagcagagc cagacggcgg ggagttggtt       720
tctggtgaag aatttgattc gattttgtcg tttgagaata tgaagagtgt gaattcgtgg       780
gggaaatcga gtttgagtta aagggtaaa gaggaagtta atgttggaga gaaacagagt        840
tcggagaacg atgacgctac ggcggagaat gcgacggcgc cgccgctatc gtttcttgag       900
aagtggctgt ttgaagaagg cgccgcgggg caagtggaag agatgatgga gttgtcgccg       960
gtgttctagc cnaaaaaaaa aaaaaaaaaa aaa                                    993

<210> SEQ ID NO 29
<211> LENGTH: 294
<212> TYPE: PRT
<213> ORGANISM: Cucumis sativus

<400> SEQUENCE: 29

Met Gly Arg Pro Pro Cys Cys Glu Lys Val Gly Ile Lys Lys Gly Pro
1               5                   10                  15

Trp Thr Pro Glu Glu Asp Ile Ile Leu Val Ser Tyr Ile Gln Gln His
```

```
                    20                  25                  30
Gly Pro Gly Asn Trp Arg Ser Val Pro Thr Asn Thr Gly Leu Leu Arg
                35                  40                  45
Cys Ser Lys Ser Cys Arg Leu Arg Trp Thr Asn Tyr Leu Arg Pro Gly
 50                  55                  60
Ile Lys Arg Gly Asn Phe Thr Pro His Glu Glu Gly Met Ile Ile His
 65                  70                  75                  80
Leu Gln Ala Leu Leu Gly Asn Lys Trp Ala Ala Ile Ala Ser Tyr Leu
                85                  90                  95
Pro Gln Arg Thr Asp Asn Asp Ile Lys Asn Tyr Trp Asn Thr His Leu
                100                 105                 110
Lys Lys Lys Leu Lys Lys Leu Asn Ser Ala Ala Val Asp Thr Pro Glu
                115                 120                 125
Pro Pro Glu Ser Ala Thr Thr Arg Phe Gln Ser Asn Asp Lys Val Pro
 130                 135                 140
Thr Ala Asp Ser Pro Ser Ser Leu Val Ser Asn Arg Ala Thr Thr Tyr
 145                 150                 155                 160
Ala Ser Ser Ala Glu Asn Ile Ser Arg Leu Leu Gln Ala Trp Met Arg
                165                 170                 175
Ser Ser Pro Glu Glu Ser Arg Arg Lys Met Ser Gly Glu Asn Ser Ile
                180                 185                 190
Ala Ala Ala Thr Gln Gln Gln Gln Pro Lys Ala Glu Pro Asp Gly
                195                 200                 205
Gly Glu Leu Val Ser Gly Glu Glu Phe Asp Ser Ile Leu Ser Phe Glu
                210                 215                 220
Asn Met Lys Ser Val Asn Ser Trp Gly Lys Ser Ser Leu Ser Tyr Lys
 225                 230                 235                 240
Gly Lys Glu Glu Val Asn Val Gly Lys Gln Ser Ser Glu Asn Asp
                245                 250                 255
Asp Ala Thr Ala Glu Asn Ala Thr Ala Pro Pro Leu Ser Phe Leu Glu
                260                 265                 270
Lys Trp Leu Phe Glu Glu Gly Ala Ala Gly Gln Val Glu Glu Met Met
                275                 280                 285
Glu Leu Ser Pro Val Phe
                290

<210> SEQ ID NO 30
<211> LENGTH: 3538
<212> TYPE: DNA
<213> ORGANISM: Cucumis sativus

<400> SEQUENCE: 30
aagctttaca aattagggtt actttattca ttttcatcca ttctctttat tgttaaattt      60
tgtacattta ttcaataata ttatatgttt attacaaatt ctcactttct tattcatacc    120
tattcactca agcctttacc atcttccttt tctatttcaa tactatttct acttcatttt    180
tcacgttttt aacatctttc tttatttctt gtccacttcg tttagggatg cctaatgtcc    240
caaatttcat ctctcgtagt aacacaaaac caatgtaatg ctacttctct ctacatttt     300 aatacaaata aagtgaaaca aaatatctat aaataaacaa atatatatat tttgttagac    360
gctgtctcaa cccatcaatt aaaaaatttt gttatatttc tactttacct actaaatttg    420
tttctcatat ttccttttta accccacaa aaaaaaatta taaaaagaa agaaaaaagc       480 taaaccctat ttaaatagct aactataaga tcttaaaatt atcctcatca gtgtatagtt    540
taattggtta ttaacttata acattatata tctatgacat atactctctc ctagctattt    600
```

```
ctcacatttt ttaacttaag aaaatagtca taacatagtc taaaattcaa acatccacat      660
gctctaattt gattaacaaa aagttagaaa tatttattta aataaaaaag actaataaat      720
atataaaatg aatgttcata cgcagaccca tttagagatg agtatgcttt cacatgctga      780
gattattttc aaaactaagg ttgtagcaat attaaatcaa taaaattatt ataaataaca      840 aaattaaccct gctcgtgttt gctgtatatg ggaggctaca aaataaatta aactaaagat     900
gattatgttt tagacatttt ttctatctgt attagtttat acatattaat tcaggagctg      960
cacaacccaa ttctattttc gttccttggt ggctgggttt ctcacaaggt tcaatagtca      1020
atattaggtt ttattggact tttaatagta tcaaacaaat ctatgtgtga acttaaaaat     1080
tgtattaaat atttagggta acctgttgcc gttttttagaa taatgtttct tcttaataca    1140
cgaaagcgta ttgtgtattc attcatttgg cgcctcacat gcttcggttg gctcgcttta    1200
gtctctgcct tctttgtata ttgtactccc cctcttccta tgccacgtgt tctgagctta    1260
acaagccacg ttgcgtgcca ttgccaaaca agtcatttta acttcacaag gtccgatttg    1320
acctccaaaa caacgacaag tttccgaaca gtcgcgaaga tcaagggtat aatcgtcttt    1380
ttgaattcta tttctctttta tttaatagtc cctctcgtgt gatagttttt aaaagatttt   1440
taaaacgtag ctgctgttta agtaaatccc agtccttcag tttgtgcttt tgtgtgtttt    1500
gtttctctga tttacggaat ttggaaataa ttctatggcg tttgtttctc aattcaatca    1560
acttccgtgc aagactctcg cactcaatcc accacaacct caattgactt ctaagccttc    1620
ggttttcccc atcgcttcga ttggggctac cgccagagcc gcggcgggga agtcactgat    1680
ctcagttagg cctgcgttca aggtccgtgc ggtgttaaac gatgacgagt ggggggagga    1740
taaggatgag aagtatggag atgattcgtc tgtggcggta gctgaaaagg aggaggaaaa    1800
gcctctggag ccatccgaga tttataaact gaagaaggcg ttggtggact cgttttacgg    1860
gaccgatcgt ggattacgag tgtccagaga tactagggcg gagattgtcg agctgattac    1920
gcaactggaa tcgaagaacc caaccccctgc tcctactgag gccctgactc tgctcaacgg   1980
caagtggatt ctagcgtaag ttctcccaat tctacctaac ttgttactag caacctgatt    2040
ggttggttga acttctaatt gtgaattggg aaaaacatcc cgaatcaata gaacctagta    2100
atttttgttt gggatgattg aaaaactgga acgagttaaa tcaaattcct ttcctgctga    2160
ctaatcgtat atctccatt caaacctctt catgaatttt taaatattgg tggtaattc      2220 ttatatatgt ttatcttgaa gatcatattt ggacgtagta tcgaccttcc atgtggcagt    2280
tgttacttca gtatcttcat gttagggaaa agtcatattg ttatgagata aactagaatg    2340
ttatgcatga gattcgatcc cgtgggccat ttagaagagg ttttatcaat cggatttggg    2400
acctgtatat gatttgtat caatttctttt gaatatggtc agttggccaa acttgcaagt    2460
tttgttatgc taaatcttag tttttcattt aaacctctcg atctctcttc attttctttg    2520
aagagaatga agagagtctc tatacaaata gcttttttac acctgataaa caggtcctaa    2580
ttttgcattt ctttttatct gttcatagtc tataacatac tagaagatga ttatgataag    2640
tttcttaata taaatgtttt tggatgtagg tacacaactt cgcgggtct gttcccgttg     2700 ttgtctagga atttgccatt ggtcaaagtg gaggaaattt cacagacaat tgattcagag    2760
aacctcaccg tccaaaactc tgtccagttt tccggtcctc tagccaccac ttccattact    2820
accaatgcaa agtttgaagt tcgaagtccc ctgcgtgtac atgtaagtct gaactgtagg    2880
aaaatttgga ttttccttgtc cgtgggtgca attccaaatc tgactttata ataaactaat   2940
agttcttttc acactcaact ttctttccag atcaaattcg aagaaggtgt cattggaact    3000
```

```
cccagctga cggattcgat agtgatacca gataatgtgg actttcttgg gcagaagatt    3060
gactttacac cattcaatgg tatcatatct tcccttcaag acactgcttc aaatgtagcc    3120
aagacgattt cgagtcaacc accaatcaag ttctcaatct caaacacgag ggtagagtct    3180
tggttgctaa ctacttatct tgatgaagat cttcgaattt cacgaggaga tggtggtagc    3240
gtgttcgtac tcctcaagga aggcagttct ttcttgtctc tctaaacacc cttactcttc    3300
tcactataaa gggttcatag gaaactgaat tattattcaa ggatgttttt aaacgtgttg    3360
tagtttctta tcaaatagtg aatgatattg ccttctgttc aaagggccag cttcaattag    3420
cttcatcttc tttaaaatca ctagttactt gaatttctgt tgagaaaata aacattgttt    3480
atcttttacc catactgtac caaaagccaa aagttaaacc aaaacgtgtg aaaagctt      3538
```

<210> SEQ ID NO 31
<211> LENGTH: 1460
<212> TYPE: DNA
<213> ORGANISM: Cucumis sativus
<220> FEATURE:
<221> NAME/KEY: misc_feature
<222> LOCATION: (1)..(1460)
<223> OTHER INFORMATION: ChrC promoter region

<400> SEQUENCE: 31

```
aagctttaca aattagggtt acttattca ttttcatcca ttctctttat tgttaaattt      60
tgtacattta ttcaataata ttatatgttt attacaaatt ctcactttct tattcatacc    120
tattcactca agcctttacc atcttccttt tctatttcaa tactatttct acttcatttt    180
tcacgttttt aacatctttc tttatttctt gtccacttcg tttagggatg cctaatgtcc    240
caaatttcat ctctcgtagt aacacaaaac caatgtaatg ctacttctct ctacattttt    300
aatacaaata aagtgaaaca aaatatctat aaataaacaa atatatatat tttgttagac    360
gctgtctcaa cccatcaatt aaaaaatttt gttatatttc tactttacct actaaatttg    420
tttctcatat ttaccttta acccccacaa aaaaaaatta taaaaagaa agaaaaaagc     480 taaaccctat ttaaatagct aactataaga tcttaaaatt atcctcatca gtgtatagtt    540
taattggtta ttaacttata acattatata tctatgacat atactctctc ctagctattt    600
ctcacatttt ttaacttaag aaaatagtca taacatagtc taaaattcaa acatccacat    660
gctctaattt gattaacaaa aagttagaaa tatttattta aataaaaaag actaataaat    720
atataaaatg aatgttcata cgcagaccca tttagagatg agtatgcttt cacatgctga    780
gattattttc aaaactaagg ttgtagcaat attaaatcaa taaaattatt ataaataaca    840 aaattaaccct gctcgtgttt gctgtatatg ggaggctaca aaataaatta aactaaagat    900
gattatgttt tagacatttt ttctatctgt attagtttat acatattaat tcaggagctg    960
cacaacccaa ttctattttc gttccttggt ggctgggttt ctcacaaggt tcaatagtca   1020
atattaggtt ttattggact tttaatagta tcaaacaaat ctatgtgtga acttaaaaat   1080
tgtattaaat atttagggta acctgttgcc gttttagaa taatgtttct tcttaataca   1140
cgaaagcgta ttgtgtattc attcatttgg cgcctcacat gcttcggttg gctcgcttta   1200
gtctctgcct tctttgtata ttgtactccc cctcttccta tgccacgtgt tctgagctta   1260
acaagccacg ttgcgtgcca ttgccaaaca agtcatttta acttcacaag gtccgatttg   1320
acctccaaaa caacgacaag tttccgaaca gtcgcgaaga tcagggtat aatcgtcttt    1380 ttgaattcta tttctcttta tttaatagtc cctctcgtgt gatagttttt aaagattttt   1440
taaaacgtag ctgctgttta                                                1460
```

```
<210> SEQ ID NO 32
<211> LENGTH: 18
<212> TYPE: DNA
<213> ORGANISM: Cucumis sativus
<220> FEATURE:
<221> NAME/KEY: misc_feature
<222> LOCATION: (1)..(18)
<223> OTHER INFORMATION: C. sativus ChrC minimal inducible promoter
      fragment

<400> SEQUENCE: 32
ctctttattt aatagtcc                                                   18

<210> SEQ ID NO 33
<211> LENGTH: 290
<212> TYPE: DNA
<213> ORGANISM: Cucumis sativus
<220> FEATURE:
<221> NAME/KEY: misc_feature
<222> LOCATION: (1)..(290)
<223> OTHER INFORMATION: C. sativus ChrC partial promoter sequence(290
      bp)

<400> SEQUENCE: 33
cgcctcacat gcttcggttg gctcgcttta gtctctgcct tctttgtatt ttgtactccc     60
cctcttcctg tgccacgtgt tctgagctta acaagccacg ttgcgtgcca ttgccaaacg    120
agtcatttta acttcacaag gtccgatttg acctccaaaa caacgacaag tttccgaaca    180
gtcgcgaaga tcaagggtat aatcgtcttt ttgaattcta tttctcttta tttaatagtc    240
cctctcgtgt gatagttttt aaaagatttt taaaacgtag ctgctgttta               290

<210> SEQ ID NO 34
<211> LENGTH: 54
<212> TYPE: DNA
<213> ORGANISM: Artificial sequence
<220> FEATURE:
<223> OTHER INFORMATION: 35S minimal promoter (TATA)

<400> SEQUENCE: 34
ccgcaagacc cttcctctat ataaggaagt tcatttcatt tggagaggac acgc           54

<210> SEQ ID NO 35
<211> LENGTH: 63
<212> TYPE: DNA
<213> ORGANISM: Artificial sequence
<220> FEATURE:
<223> OTHER INFORMATION: MG1 mutant of the cucumber ChrC promoter

<400> SEQUENCE: 35
gacgtatcta acaacgacaa gtttccgaac agtcgcgaag atcaagggta taatcgtctt     60
ttt                                                                   63

<210> SEQ ID NO 36
<211> LENGTH: 63
<212> TYPE: DNA
<213> ORGANISM: Artificial sequence
<220> FEATURE:
<223> OTHER INFORMATION: MG2 mutant of the cucumber ChrC promoter

<400> SEQUENCE: 36
gacctcgtat ctaacgacaa gtttccgaac agtcgcgaag atcaagggta taatcgtctt     60
ttt                                                                   63
```

```
<210> SEQ ID NO 37
<211> LENGTH: 63
<212> TYPE: DNA
<213> ORGANISM: Artificial sequence
<220> FEATURE:
<223> OTHER INFORMATION: MG3 mutant of the cucumber ChrC promoter

<400> SEQUENCE: 37
gacctccaag tatctgacaa gtttccgaac agtcgcgaag atcaagggta taatcgtctt      60
ttt                                                                   63
```